(12) United States Patent
Qiu et al.

(10) Patent No.: US 11,099,300 B2
(45) Date of Patent: Aug. 24, 2021

(54) METHOD FOR PRODUCING COATED SILICONE HYDROGEL CONTACT LENSES

(71) Applicant: Alcon Inc., Fribourg (CH)

(72) Inventors: Yongxing Qiu, Suwanee, GA (US); Hyeju Kim, Paju-si (KR); Ciara Dauenhauer, Cumming, GA (US)

(73) Assignee: Alcon Inc., Fribourg (CH)

( * ) Notice: Subject to any disclaimer, the term of this patent is extended or adjusted under 35 U.S.C. 154(b) by 217 days.

(21) Appl. No.: 16/426,451

(22) Filed: May 30, 2019

(65) Prior Publication Data

US 2020/0174160 A1 Jun. 4, 2020

Related U.S. Application Data

(60) Provisional application No. 62/774,431, filed on Dec. 3, 2018.

(51) Int. Cl.
| | | |
|---|---|---|
| *G02B 1/04* | (2006.01) | |
| *C09D 133/08* | (2006.01) | |
| *G02B 1/10* | (2015.01) | |
| *A61L 12/04* | (2006.01) | |

(52) U.S. Cl.
CPC .............. *G02B 1/043* (2013.01); *A61L 12/04* (2013.01); *C09D 133/08* (2013.01); *G02B 1/10* (2013.01); *G02B 2207/109* (2013.01)

(58) Field of Classification Search
CPC .................................................... G02B 1/043
See application file for complete search history.

(56) References Cited

U.S. PATENT DOCUMENTS

| | | |
|---|---|---|
| 4,136,250 A | 1/1979 | Mueller |
| 4,153,641 A | 5/1979 | Deichert et al. |
| 4,182,822 A | 1/1980 | Chang |
| 4,189,546 A | 2/1980 | Deichert et al. |
| 4,254,248 A | 3/1981 | Friends et al. |
| 4,259,467 A | 3/1981 | Keogh et al. |
| 4,260,725 A | 4/1981 | Keogh et al. |
| 4,261,875 A | 4/1981 | LeBoeuf |
| 4,276,402 A | 6/1981 | Chromecek et al. |
| 4,327,203 A | 4/1982 | Deichert et al. |
| 4,341,889 A | 7/1982 | Deichert et al. |
| 4,343,927 A | 8/1982 | Chang |
| 4,355,147 A | 10/1982 | Deichert et al. |
| 4,444,711 A | 4/1984 | Schad |
| 4,460,534 A | 7/1984 | Boehm et al. |
| 4,486,577 A | 12/1984 | Mueller et al. |
| 4,543,398 A | 9/1985 | Bany et al. |
| 4,605,712 A | 8/1986 | Mueller et al. |
| 4,661,575 A | 4/1987 | Tom |
| 4,684,538 A | 8/1987 | Klemarczyk |
| 4,703,097 A | 10/1987 | Wingler et al. |
| 4,833,218 A | 5/1989 | Lee |
| 4,837,289 A | 6/1989 | Mueller et al. |
| 4,954,586 A | 9/1990 | Toyoshima et al. |
| 4,954,587 A | 9/1990 | Mueller |
| 5,010,141 A | 4/1991 | Mueller |
| 5,034,461 A | 7/1991 | Lai et al. |
| 5,039,761 A | 8/1991 | Ono et al. |
| 5,070,170 A | 12/1991 | Robertson et al. |
| 5,079,319 A | 1/1992 | Mueller |
| 5,346,946 A | 9/1994 | Yokoyama et al. |
| 5,358,995 A | 10/1994 | Lai et al. |
| 5,387,632 A | 2/1995 | Lai et al. |
| 5,416,132 A | 5/1995 | Yokoyama et al. |
| 5,449,729 A | 9/1995 | Lai |
| 5,451,617 A | 9/1995 | Lai et al. |
| 5,486,579 A | 1/1996 | Lai et al. |
| 5,760,100 A | 6/1998 | Nicolson et al. |
| 5,843,346 A | 12/1998 | Morrill |
| 5,858,937 A | 1/1999 | Richard |
| 5,894,002 A | 4/1999 | Boneberger et al. |
| 5,962,548 A | 10/1999 | Vanderlaan et al. |
| 5,981,675 A | 11/1999 | Valint et al. |
| 6,039,913 A | 3/2000 | Hirt et al. |
| 6,218,508 B1 | 4/2001 | Kragh et al. |
| 6,367,929 B1 | 4/2002 | Maiden et al. |
| 6,762,264 B2 | 7/2004 | Kuenzler et al. |
| 6,822,016 B2 | 11/2004 | McCabe et al. |
| 6,867,245 B2 | 3/2005 | Iwata et al. |
| 7,052,131 B2 | 5/2006 | McCabe et al. |
| 7,091,283 B2 | 8/2006 | Mueller et al. |
| 7,214,809 B2 | 5/2007 | Zanini et al. |
| 7,238,750 B2 | 7/2007 | Mueller et al. |
| 7,249,848 B2 | 7/2007 | Laredo et al. |
| 7,268,189 B2 | 9/2007 | Mueller et al. |
| 7,268,198 B2 | 9/2007 | Kunzler |
| 7,423,074 B2 | 9/2008 | Lai |
| 7,521,519 B1 | 4/2009 | Hirt et al. |
| 7,540,609 B2 | 6/2009 | Chen |
| 7,572,841 B2 | 8/2009 | Chen |
| 7,605,190 B2 | 10/2009 | Moszner et al. |
| 7,750,079 B2 | 7/2010 | Almond |
| 7,915,323 B2 | 3/2011 | Awasthi et al. |
| 7,934,830 B2 | 5/2011 | Blackwell |
| 8,231,218 B2 | 7/2012 | Hong |

(Continued)

FOREIGN PATENT DOCUMENTS

EP 1465931 B1 8/2007

*Primary Examiner* — Michael F Pepitone
(74) *Attorney, Agent, or Firm* — Jian Zhou

(57) ABSTRACT

The invention is generally related to a method for producing, in a consistent manner, SiHy contact lenses each having an intact durable coating thereon, wherein the coating is a hydrogel coating formed by covalently attached a hydrophilic polymeric material onto a base coating of a polyanionic polymer on a SiHy contact lens. In this method, the base coating is formed by having two solution coating steps separated by at least one rinsing step with a buffered saline or pH controlled solution. The durability of the hydrogel coatings on resultant silicone hydrogel contact lenses can be improved significantly and will not vary with the optical power (i.e., the center thickness) of the SiHy contact lens under coating.

20 Claims, 1 Drawing Sheet

(56) References Cited

U.S. PATENT DOCUMENTS

| | | |
|---|---|---|
| 8,367,746 B2 | 2/2013 | Manesis et al. |
| 8,383,744 B2 | 2/2013 | Justynska |
| 8,415,405 B2 | 4/2013 | Maggio |
| 8,420,711 B2 | 4/2013 | Awasthi et al. |
| 8,445,614 B2 | 5/2013 | Francis |
| 8,475,529 B2 | 7/2013 | Clarke |
| 8,480,227 B2 | 7/2013 | Qiu et al. |
| 8,481,662 B2 | 7/2013 | Liu |
| 8,487,058 B2 | 7/2013 | Liu |
| 8,513,325 B2 | 8/2013 | Liu |
| 8,529,057 B2 | 9/2013 | Qiu et al. |
| 8,614,261 B2 | 12/2013 | Iwata et al. |
| 8,642,712 B2 | 2/2014 | Chang |
| 8,658,748 B2 | 2/2014 | Liu |
| 8,703,891 B2 | 4/2014 | Broad |
| 8,820,928 B2 | 9/2014 | Back |
| 8,865,789 B2 | 10/2014 | Yao |
| 8,937,110 B2 | 1/2015 | Alli |
| 8,937,111 B2 | 1/2015 | Alli |
| 8,993,651 B2 | 3/2015 | Chang et al. |
| 9,057,821 B2 | 6/2015 | Broad |
| 9,057,822 B2 | 6/2015 | Liu |
| 9,097,840 B2 | 8/2015 | Chang |
| 9,103,965 B2 | 8/2015 | Chang |
| 9,121,998 B2 | 9/2015 | Chen |
| 9,125,808 B2 | 9/2015 | Alli |
| 9,127,099 B2 | 9/2015 | Iwakiri |
| 9,140,825 B2 | 9/2015 | Alli |
| 9,140,908 B2 | 9/2015 | Ge |
| 9,156,934 B2 | 10/2015 | Alli |
| 9,164,298 B2 | 10/2015 | Hong |
| 9,170,349 B2 | 10/2015 | Mahadevan |
| 9,188,702 B2 | 11/2015 | Vanderlaan |
| 9,217,813 B2 | 12/2015 | Liu |
| 9,296,159 B2 | 3/2016 | Zheng |
| 9,322,959 B2 | 4/2016 | Ueyama |
| 9,322,960 B2 | 4/2016 | Broad |
| 9,360,594 B2 | 6/2016 | Liu |
| 9,475,827 B2 | 10/2016 | Chang |
| 9,529,119 B2 | 12/2016 | Imafuku |
| 10,081,697 B2 | 9/2018 | Huang |
| 2008/0015315 A1 | 1/2008 | Chang |
| 2008/0143003 A1 | 6/2008 | Phelan |
| 2008/0143958 A1 | 6/2008 | Medina |
| 2008/0231798 A1 | 9/2008 | Zhou |
| 2008/0234457 A1 | 9/2008 | Zhou |
| 2012/0026457 A1 | 2/2012 | Qiu |
| 2012/0088843 A1 | 4/2012 | Chang |
| 2012/0088844 A1 | 4/2012 | Kuyu |
| 2012/0244088 A1 | 9/2012 | Saxena |
| 2012/0245249 A1 | 9/2012 | Saxena |
| 2013/0337160 A1 | 12/2013 | Holland |
| 2015/0166205 A1 | 6/2015 | Qiu |
| 2016/0061995 A1 | 3/2016 | Chang |
| 2016/0326046 A1 | 11/2016 | Quinter |
| 2017/0165932 A1* | 6/2017 | Qian ................ B29D 11/00038 |
| 2018/0100038 A1 | 4/2018 | Jing |
| 2018/0100053 A1 | 4/2018 | Jing |
| 2018/0355112 A1 | 12/2018 | Zhang |
| 2018/0356562 A1 | 12/2018 | Wu |

\* cited by examiner

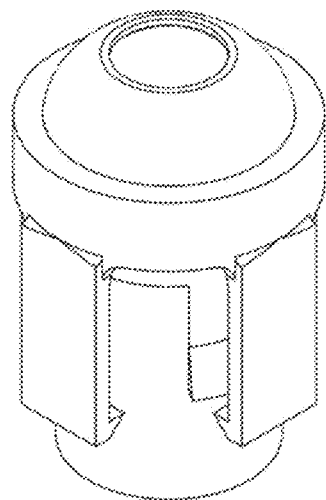
A
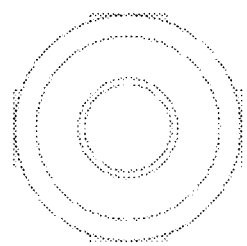
B
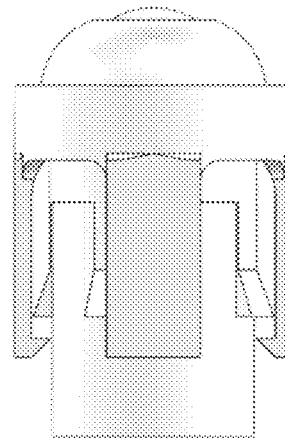
C
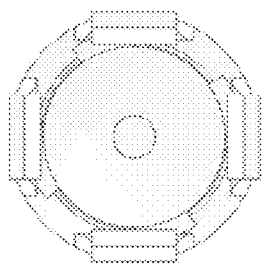
D
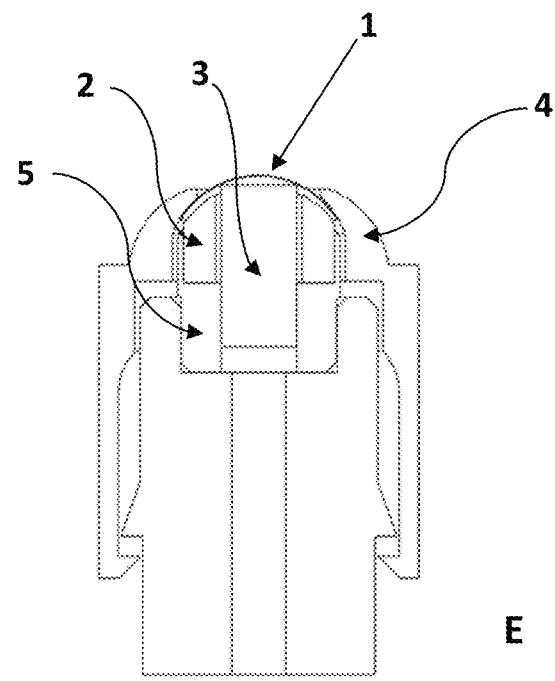
E

METHOD FOR PRODUCING COATED SILICONE HYDROGEL CONTACT LENSES

This application claims the benefit under 35 USC § 119 (e) of U.S. provisional application No. 62/774,431 filed 3 Dec. 2018, herein incorporated by reference in its entirety.

The present invention generally relates to a method for producing silicone hydrogel contact lenses having a stable and intact coating thereon. In addition, the present invention provides silicone hydrogel contact lenses produced according to the method of the invention.

BACKGROUND

A new class of soft contact lenses, water gradient silicone hydrogel contact lenses, have been developed and successfully introduced as daily-disposable contact lenses, DAILIES® TOTAL1® (Alcon) in the market. This new class of silicone hydrogel contact lenses is characterized by having a water-gradient structural configuration, an increase from 33% to over 80% water content from core to surface (U.S. Pat. No. 8,480,227). This unique design can deliver a highly-lubricious and extremely-soft, water-rich lens surface that in turn provide superior wearing comfort to patients. Such soft contact lenses can be produced according to a cost-effective approach that is described in U.S. Pat. No. 8,529,057 and involves a step of crosslinking and covalently attaching of a water-soluble highly-branched hydrophilic polymeric material onto lens surfaces to form surface gels.

According to U.S. Pat. No. 8,529,057, contact lenses having a water-gradient structural configuration and a soft, water-rich, and lubricious surface can be produced by forming an anchoring layer on each contact lens by dipping the contact lenses in a coating solution of a polyanionic polymer and then covalently attaching a water-soluble highly-branched hydrophilic polymeric material onto the anchoring layer directly in a lens package during autoclave. The water-soluble highly-branched hydrophilic polymeric material is prepared by partially reacting a polyamidoamine-epichlorohydrin (PAE) with a wetting agent, at various concentration ratio of PAE to the wetting agent and at a reaction temperature for a given reaction time, to achieve a desired lubricity of the surface gels while minimizing or eliminating surface defects (e.g., surface cracking, etc.).

Although the newly-developed water-gradient silicone hydrogel contact lenses can provide superior wearing comfort to patients due to their extremely-soft, water-rich and relatively-thick hydrogel coatings, they may not be compatible with all lens care solutions in the market. For instance, these new contact lenses may not be compatible with some multipurpose lens care solutions existed in the market, because they are likely to uptake polycationic antimicrobials (e.g., polyhexamethylene biguanide, Polyquaternium-1 (aka PolyQuad®), or the like, which are commonly found in most multipurpose lens care solutions), due to the presence of the anchoring layer of a polyanionic material. Those polycationic antimicrobials adsorbed by the contact lenses may be released into the eye and may cause undesirable clinical symptoms in some persons, such as diffuse corneal staining and product intolerance, when the lenses are worn by patients. Because of the incompatibility with some multipurpose lens care solutions, the newly-developed water gradient silicone hydrogel contact lenses may not be suitable to be used as weekly or monthly disposable contact lenses which must be cleaned and disinfected almost on the daily basis with a lens care solution.

US2015/0166205A1 and US2016/0326046A1 discloses approaches for reducing water gradient contact lenses' susceptibility to deposition and accumulation of polycationic antimicrobials by adding one step involving use of a polyamidoamine-epichlorohydrin (PAE). However, there are some disadvantages associated with those approaches. For example, although the susceptibility to deposition and accumulation of polycationic antimicrobials of a contact lens with a hydrogel coating can be reduced according to those approaches, the lubricity, wettability and/or hydrophilicity of the resultant contact lens will be reduced simultaneously and the reduction in deposition and accumulation of polycationic antimicrobials may not be sufficient to render the contact lenses compatible with all multipurpose lens care solutions in the market. Further, the contact lenses obtained according to those approaches may not be able to survive digital rubbings required in the lens care regimes involving a multipurpose lens care solution or accidental lens inversion during lens manufacturing or handling, because the digital rubbings of the contact lenses and lens inversion can cause damages to the hydrogel coating on the contact lenses as evidenced by cracking lines visible under dark field after the contact lens is inversed or rubbed between fingers.

Therefore, there is still a need for a method for producing silicone hydrogel contact lenses with a durable non-silicone hydrogel coating which has a minimized susceptibility to high deposition and accumulation of positively charged antimicrobials. There is also a need for silicone hydrogel contact lenses with such a durable coating thereon.

SUMMARY OF THE INVENTION

The invention provides a method for producing coated silicone hydrogel contact lenses each having a hydrogel coating thereon, the method of invention comprising the steps of: (1) obtaining a preformed silicone hydrogel contact lens; (2) forming a base coating on the preformed silicone hydrogel contact lens according to a solution-coating procedure to form a treated silicone hydrogel contact lens having the base coating thereon, wherein the solution-coating procedure comprises the sub-steps of (a) contacting the preformed silicone hydrogel contact lens with a first coating solution for a first coating period of time, wherein the first coating solution has a first pH and comprises from about 0.001% to about 5.0% by weight of a first polyanionic polymer, (b) rinsing the preformed silicone hydrogel contact lens obtained in sub-step (a) with a first buffered saline having a second pH for a first rinsing period of time, (c) optionally rinsing the preformed silicone hydrogel contact lens obtained in sub-step (b) with water, one or more organic solvent miscible with water, or a mixture thereof for a second rinsing period of time, (d) contacting the preformed silicone hydrogel contact lens obtained in sub-step (b) or (c) with a second coating solution for a second coating period of time, wherein the second coating solution has a third pH and comprises from about 0.001% to about 5.0% by weight of a second polyanionic polymer, (e) rinsing the preformed silicone hydrogel contact lens obtained in sub-step (d) with a second buffered saline having a fourth pH for a third rinsing period of time, (f) optionally rinsing the preformed silicone hydrogel contact lens obtained in sub-step (e) with water, one or more organic solvent miscible with water, or a mixture thereof for a fourth rinsing period of time wherein the first and second polyanionic polymer independent of each other are a homo- or copolymer of acrylic acid or $C_1$-$C_3$ alkylacrylic acid, wherein the first pH and the third pH independent of each other are from 0 to about 4.5, wherein the second pH and the fourth pH independent of each other are from about 6.5 to about 10 and (3) heating the treated silicone hydrogel contact lens having the base coating thereon in an aqueous solution having a pH from about 6.8 to about 9.5 and including a water-soluble, thermally-crosslinkable hydrophilic polymeric material at a temperature from about 60° C. to about 140° C. to form a coated silicone hydrogel contact lens have a hydrogel coating thereon, wherein the hydrogel coating is covalently attached onto the base coating, wherein the coated silicone hydrogel contact lens having the hydrogel coating thereon can pass Sudan Black staining test after being subjected to 30 cycles of digital rubbing treatment or after simulated abrasion cycling treatment.

These and other aspects of the invention will become apparent from the following description of the presently preferred embodiments. The detailed description is merely illustrative of the invention and does not limit the scope of the invention, which is defined by the appended claims and equivalents thereof. As would be obvious to one skilled in the art, many variations and modifications of the invention may be effectuated without departing from the spirit and scope of the novel concepts of the disclosure.

BRIEF DESCRIPTION OF THE DRAWINGS

FIG. 1 schematically illustrates a lens holder for performing the simulated abrasion cycling treatment of a lens in order to determine the long-lasting lubricity and/or long-lasting wettability of a contact lens of the invention: A—Perspective view; B—Top view; C—Side view; D—Bottom view; and E—sectional view.

DETAILED DESCRIPTION OF EMBODIMENTS OF THE INVENTION

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term. The nomenclature used herein and the laboratory procedures described below are those well-known and commonly employed in the art.

"About" as used herein in this application means that a number, which is referred to as "about", comprises the recited number plus or minus 1-10% of that recited number.

"Contact Lens" refers to a structure that can be placed on or within a wearer's eye. A contact lens can correct, improve, or alter a user's eyesight, but that need not be the case.

A "hydrogel contact lens" refers to a contact lens comprising a non-silicone hydrogel as lens bulk material.

A "silicone hydrogel contact lens" refers to a contact lens comprising a silicone hydrogel (designated as "SiHy" in this application) as lens bulk material.

A "hydrogel" or "hydrogel material" refers to a crosslinked polymeric material which is insoluble in water, but can hold at least 10 percent by weight of water in its three-dimensional polymer networks (i.e., polymer matrix) when it is fully hydrated.

As used in this application, the term "non-silicone hydrogel" refers to a hydrogel that is theoretically free of silicon.

As used in this application, the term "silicone hydrogel" or "SiHy" refers to a hydrogel containing silicone.

"Hydrophilic," as used herein, describes a material or portion thereof that will more readily associate with water than with lipids.

A "vinylic monomer" refers to a compound that has one sole ethylenically unsaturated group, is soluble in a solvent, and can be polymerized actinically or thermally.

The term "soluble", in reference to a compound or material in a solvent, means that the compound or material can be dissolved in the solvent to give a solution with a concentration of at least about 0.05% by weight at room temperature (i.e., from about 22° C. to about 28° C.).

The term "insoluble", in reference to a compound or material in a solvent, means that the compound or material can be dissolved in the solvent to give a solution with a concentration of less than 0.005% by weight at room temperature (as defined above).

As used in this application, the term "ethylenically unsaturated group" is employed herein in a broad sense and is intended to encompass any groups containing at least one >C=C< group. Exemplary ethylenically unsaturated groups include without limitation (meth)acryloyl

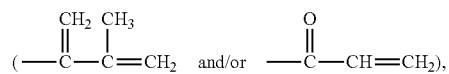

allyl, vinyl, styrenyl, or other C=C containing groups.

The term "(meth)acrylamide" refers to methacrylamide and/or acrylamide.

The term "(meth)acrylate" refers to methacrylate and/or acrylate.

As used herein, "actinically" in reference to curing, crosslinking or polymerizing of a polymerizable composition, a prepolymer or a material means that the curing (e.g., crosslinked and/or polymerized) is performed by actinic irradiation, such as, for example, UV/visible irradiation, ionizing radiation (e.g. gamma ray or X-ray irradiation), microwave irradiation, and the like. Thermal curing or actinic curing methods are well-known to a person skilled in the art.

A "hydrophilic vinylic monomer", as used herein, refers to a vinylic monomer which as a homopolymer typically yields a polymer that is water-soluble or can absorb at least 10 percent by weight of water.

A "hydrophobic vinylic monomer", as used herein, refers to a vinylic monomer which as a homopolymer typically yields a polymer that is insoluble in water and can absorb less than 10 percent by weight of water.

A "blending vinylic monomer" refers to a vinylic monomer capable of dissolving both hydrophilic and hydrophobic components of a polymerizable composition to form a solution.

An "acrylic monomer" refers to a vinylic monomer having one sole (meth)acryloyl group.

An "N-vinyl amide monomer" refers to an amide compound having a vinyl group (—CH=CH$_2$) that is directly attached to the nitrogen atom of the amide group.

A "macromer" or "prepolymer" refers to a compound or polymer comprising ethylenically unsaturated groups and having a number average molecular weight of greater than 700 Daltons.

As used in this application, the term "vinylic crosslinker" refers to a compound having at least two ethylenically unsaturated groups. A "vinylic crosslinking agent" refers to a subclass of vinylic crosslinkers each having a number average molecular weight of 700 Daltons or less.

As used in this application, the term "polymer" means a material formed by polymerizing or crosslinking one or more monomers, macromers, prepolymers and/or combinations thereof.

As used in this application, the term "molecular weight" of a polymeric material (including monomeric or macromeric materials) refers to the number average molecular weight unless otherwise specifically noted or unless testing conditions indicate otherwise.

A "polysiloxane segment" refers to a polymer chain consisting of at least three consecutively- and directly-linked siloxane units (divalent radical) each independent of one another having a formula of

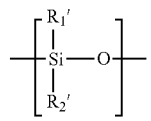

in which $R_1'$ and $R_2'$ are two substituents independently selected from the group consisting of $C_1$-$C_{10}$ alkyl, $C_1$-$C_4$ alkyl- or $C_1$-$C_4$-alkoxy-substituted phenyl, $C_1$-$C_{10}$ fluoroalkyl, $C_1$-$C_{10}$ fluoroether, $C_6$-$C_{18}$ aryl radical, -alk-$(OC_2H_4)_{y1}$—$OR^0$ (in which alk is $C_1$-$C_6$ alkyl diradical, $R^0$ is H or $C_1$-$C_4$ alkyl and 71 is an integer from 1 to 10), a $C_2$-$C_{40}$ organic radical having at least one functional group selected from the group consisting of hydroxyl group (—OH), carboxyl group (—COOH), —$NR_3'R_4'$, amino linkages of —$NR_3'$—, amide linkages of —$CONR_3'$—, amide of —$CONR_3'R_4'$, urethane linkages of —OCONH—, and $C_1$-$C_4$ alkoxy group, or a linear hydrophilic polymer chain, in which $R_3'$ and $R_4'$ independent of each other are hydrogen or a $C_1$-$C_{15}$ alkyl.

A "polysiloxane vinylic monomer" refers to a compound comprising at least one polysiloxane segment and one sole ethylenically-unsaturated group.

A "polysiloxane vinylic crosslinker" refers to a compound comprising at least one polysiloxane segment and at least two ethylenically-unsaturated groups.

A "chain-extended polysiloxane vinylic crosslinker" refers to a compound comprising at least two ethylenically-unsaturated groups and at least two polysiloxane segments each pair of which is linked by one divalent radical.

A "polycarbosiloxane" refers to a compound containing at least one polycarbosiloxane segment which is a polymer chain consisting of at least three consecutively- and directly-linked siloxane units (divalent radical) each independent of one another having a formula of

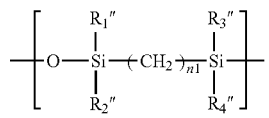

in which n1 is an integer of 2 or 3, $R_1''$, $R_2''$, $R_3''$, and $R_4''$ independent of one another are a $C_1$-$C_6$ alkyl radical (preferably methyl).

A "polycarbosiloxane vinylic monomer" refers to a compound comprising at least one polycarbosiloxane segment and one sole ethylenically-unsaturated group.

A "polycarbosiloxane vinylic crosslinker" refers to a compound comprising at least one polycarbosiloxane segment and at least two ethylenically-unsaturated groups.

The term "fluid" as used herein indicates that a material is capable of flowing like a liquid.

As used in this application, the term "clear" in reference to a polymerizable composition means that the polymerizable composition is a transparent solution or liquid mixture (i.e., having a light transmissibility of 85% or greater in the range between 400 to 700 nm).

The term "alkyl" refers to a monovalent radical obtained by removing a hydrogen atom from a linear or branched alkane compound. An alkyl group (radical) forms one bond with one other group in an organic compound.

The term "alkylene divalent group" or "alkylene diradical" or "alkyl diradical" interchangeably refers to a divalent radical obtained by removing one hydrogen atom from an alkyl. An alkylene divalent group forms two bonds with other groups in an organic compound.

The term "alkyl triradical" refers to a trivalent radical obtained by removing two hydrogen atoms from an alkyl. An alkyl triradical forms three bonds with other groups in an organic compound.

The term "alkoxy" or "alkoxyl" refers to a monovalent radical obtained by removing the hydrogen atom from the hydroxyl group of a linear or branched alkyl alcohol. An alkoxy group (radical) forms one bond with one other group in an organic compound.

As used in this application, the term "amino group" refers to a primary or secondary amino group of formula —NHR', where R' is hydrogen or a $C_1$-$C_{20}$ unsubstituted or substituted, linear or branched alkyl group, unless otherwise specifically noted.

In this application, the term "substituted" in reference to an alkyl diradical or an alkyl radical means that the alkyl diradical or the alkyl radical comprises at least one substituent which replaces one hydrogen atom of the alkyl diradical or the alkyl radical and is selected from the group consisting of hydroxy (—OH), carboxy (—COOH), —$NH_2$, sulfhydryl (—SH), $C_1$-$C_4$ alkyl, $C_1$-$C_4$ alkoxy, $C_1$-$C_4$ alkylthio (alkyl sulfide), $C_1$-$C_4$ acylamino, $C_1$-$C_4$ alkylamino, di-$C_1$-$C_4$ alkylamino, halogen atom (Br or Cl), and combinations thereof.

In this application, an "oxazoline" refers to a compound of

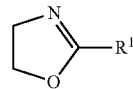

in which: $R^1$ is hydrogen, methyl, ethyl, N-pyrrolidonylmethyl, N-pyrrolidonylethyl, N-pyrrolidonylpropyl, or a monovalent radical of -alk-$(OC_2H_4)_{m3}$—OR in which alk is $C_1$-$C_4$ alkyl diradical; R" is $C_1$-$C_4$ alkyl (preferably methyl); and m3 is an integer from 1 to 10 (preferably 1 to 5).

In this application, the term "polyoxazoline" refers to a polymer or polymer segment of

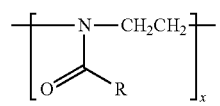

in which: $R^1$ is hydrogen, methyl, ethyl, N-pyrrolidinylmethyl, N-pyrrolidinylethyl, N-pyrrolidinylpropyl, or a monovalent radical of -alk-$(OC_2H_4)_{m3}$—OR in which alk is $C_1$-$C_4$ alkyl diradical; R" is $C_1$-$C_4$ alkyl (preferably methyl); m3 is an integer from 1 to 10 (preferably 1 to 5); x is an integer from 5 to 500.

In this application, the term "poly(2-oxazoline-co-ethyleneimine)" refers to a statistical copolymer or a polymer segment thereof having a formula of

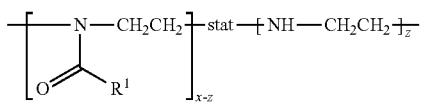

in which: $R^1$ is hydrogen, methyl, ethyl, N-pyrrolidonylmethyl, N-pyrrolidonylethyl, N-pyrrolidonylpropyl, or a monovalent radical of -alk-$(OC_2H_4)_{m3}$—OR' in which alk is $C_1$-$C_4$ alkyl diradical; R" is $C_1$-$C_4$ alkyl (preferably methyl); m3 is an integer from 1 to 10 (preferably 1 to 5); x is an integer from 5 to 500; z is an integer equal to or less than x. A poly(2-oxazoline-co-ethyleneimine) is obtained by hydrolyzing a polyoxazoline.

In this application, the term "poly(2-oxazoline-co-ethyleneimine)-epichlorohydrm" refers to a polymer obtained by reacting a poly(2-oxazoline-co-ethyleneimine) with epichlorohydrin to convert all or substantial percentage (≥90%) of the secondary amine groups of the poly(2-oxazoline-co-ethyleneimine) into azetidinium groups. Examples of poly (2-oxazoline-co-ethyleneimine)-epichlorohydrin are disclosed in a copending U.S. pat. Appl. No. 2016/0061995A1.

An "epichlorohydrin-functionalized polyamine" or "epichlorohydrin-functionalized polyamidoamine" refers to a polymer obtained by reacting a polyamine or polyamidoamine with epichlorohydrin to convert all or a substantial percentage of the secondary amine groups of the polyamine or polyamidoamine into azetidinium groups.

The term "polyamidoamine-epichlorohydrin" refers to an epichlorohydrin-functionalized adipic acid-diethylenetriamine copolymer.

In this application the term "azetidinium" or "3-hydroxyazetidinium" refers to a positively-charged, divalent radical (or group or moiety) of

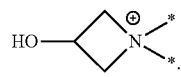

The term "thermally-crosslinkable" in reference to a polymeric material or a functional group means that the polymeric material or the functional group can undergo a crosslinking (or coupling) reaction with another material or functional group at a relatively-elevated temperature (from about 40° C. to about 140° C.), whereas the polymeric material or functional group cannot undergo the same crosslinking reaction (or coupling reaction) with another material or functional group at a temperature of from about 5° C. to about 15° C., to an extend detectable for a period of about one hour.

The term "azlactone" refers to a mono-valent radical of formula

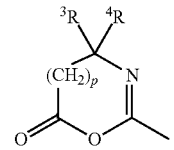

in which p is 0 or 1; $^3R$ and $^4R$ independently of each other is $C_1$-$C_8$ alkyl (preferably methyl).

As used in this application, the term "phosphorylcholine" refers to a zwitterionic group of

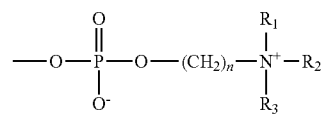

in which n is an integer of 1 to 5 and $R_1$, $R_2$ and $R_3$ independently of each other are $C_1$-$C_8$ alkyl or $C_1$-$C_8$ hydroxyalkyl.

As used in this application, the term "reactive vinylic monomer" refers to any vinylic monomer having at least one reactive functional group selected from the group consisting of carboxyl group, primary amino group, and secondary amino group.

As used in this application, the term "non-reactive vinylic monomer" refers to any vinylic monomer (either hydrophilic or hydrophobic vinylic monomer) free of carboxyl group, primary amino group, secondary amino group, epoxide group, isocyanate group, azlactone group, or aziridine group.

A free radical initiator can be either a photoinitiator or a thermal initiator. A "photoinitiator" refers to a chemical that initiates free radical crosslinking/polymerizing reaction by the use of light. A "thermal initiator" refers to a chemical that initiates radical crosslinking/polymerizing reaction by the use of heat energy.

The intrinsic "oxygen permeability", $Dk_i$, of a material is the rate at which oxygen will pass through a material. As used in this application, the term "oxygen permeability (Dk)" in reference to a hydrogel (silicone or non-silicone) or a contact lens means a corrected oxygen permeability ($Dk_c$) which is measured at about 34-35° C. and corrected for the surface resistance to oxygen flux caused by the boundary layer effect according to the procedures described in Example 1 of U.S. patent application publication No. 2012/0026457 A1. Oxygen permeability is conventionally expressed in units of barrers, where "barrer" is defined as $[(cm^3 \text{ oxygen})(mm)/(cm^2)(sec)(mm \text{ Hg})] \times 10^{-10}$.

The "oxygen transmissibility", Dk/t, of a lens or material is the rate at which oxygen will pass through a specific lens or material with an average thickness of t [in units of mm] over the area being measured. Oxygen transmissibility is conventionally expressed in units of barrers/mm, where "barrers/mm" is defined as $[(cm^3 \text{ oxygen})/(cm^2)(sec)(mm \text{ Hg})] \times 10^{-9}$.

"Ophthalmically compatible", as used herein, refers to a material or surface of a material which may be in intimate contact with the ocular environment for an extended period of time without significantly damaging the ocular environment and without significant user discomfort.

The term "ophthalmically safe" with respect to a packaging solution for sterilizing and storing contact lenses is meant that a contact lens stored in the solution is safe for direct placement on the eye without rinsing after autoclave and that the solution is safe and sufficiently comfortable for daily contact with the eye via a contact lens. An ophthalmically-safe packaging solution after autoclave has a tonicity and a pH that are compatible with the eye and is substantially free of ocularly irritating or ocularly cytotoxic materials according to international ISO standards and U.S. FDA regulations.

The term "modulus" or "elastic modulus" in reference to a contact lens or a material means the tensile modulus or Young's modulus which is a measure of the stiffness of a contact lens or a material. The modulus can be measured using a method in accordance with ANSI Z80.20 standard. A person skilled in the art knows well how to determine the elastic modulus of a SiHy material or a contact lens. For example, all commercial contact lenses have reported values of elastic modulus.

As used in this application, the term "equilibrium water content" in reference to a contact lens or a polymeric material means the amount (expressed as percent by weight) of water present in the contact lens or the polymeric material when being fully hydrated (equilibrated) in saline solution (ca. 0.79 wt % NaCl) and determined at room temperature (as defined above).

As used in this application, the term "crosslinked coating" or "hydrogel coating" or "hydrogel layer" on a contact lens interchangeably is used to describe a crosslinked polymeric material having a three-dimensional network that can contain water when fully hydrated. The three-dimensional network of a crosslinked polymeric material can be formed by crosslinking of two or more linear or branched polymers through crosslinkages.

As used in this application, the term "polyquarternium-1 uptake" or "PU" in reference to a contact lens means the amount of polyquaternium-1 absorbed by the contact lens, as measured according to the procedure described in Example 1.

As used in this application, the term "long-lasting surface hydrophilicity and wettability" in reference to a contact lens means that the contact lens has a water-break-up time (WBUT) of at least 10 seconds after 30 cycles of digital rubbing treatment or after simulated abrasion cycling treatment. WBUT determination, cycle of digital rubbing treatment, and simulated abrasion cycling treatment of a contact lens are performed according to the procedures described in Example 1.

As used in this application, the term "long-lasting lubricity" in reference to a contact lens means that the contact lens has a friction rating of about 2.0 or lower after 30 cycles of digital rubbing treatment or after simulated abrasion cycling treatment. Friction rating determination, cycle of digital rubbing treatment, and simulated abrasion cycling treatment of a contact lens are performed according to the procedures described in Example 1.

As used in this application, the term "durability" or "durable" in reference to a hydrogel coating on a coated SiHy contact lens or to a coated SiHy contact lens having a hydrogel coating thereon means that the hydrogel coating on the coated SiHy contact lens remains intact as shown by having no Sudan Black staining in Sudan Black stain test carried out after the coated SiHy contact lens has been subjected to 30 cycles of digital rubbing treatment or after simulated abrasion cycling treatment. Sudan Black Stain test is carried out according to the procedures described in Example 1.

As used in this application, the term "pass Sudan Black staining test" in reference to a coated SiHy contact lens having a hydrogel coating thereon means that when being subjected to Sudan Black Stain test, the coated SiHy contact lens having a hydrogel coating thereon is free of staining under a naked eye's observation.

As used in this application, the term "30 cycles of digital rubbing treatment" or "n cycles of digital rubbing treatment" means that contact lenses are subjected to 30 or n repetitions of a digital rubbing procedure which essentially consists of digitally rubbing (wearing disposable powder-free latex gloves) contact lenses with RENU® multi-purpose lens care solution (or an equivalent, e.g., a multi-purpose lens care solution disclosed in Table I of U.S. Pat. No. 5,858,937 for 20 seconds and then rinsing the digitally-rubbed contact lenses with a phosphate-buffered saline for at least 20 seconds. The 30 or n cycles of digital rubbing treatment can reasonably imitate daily cleaning and disinfecting in a 30-day or n-day lens care regime.

In accordance with the invention, WBUT and $WCA_{cb}$ are measured according to the procedures described in Example 1.

An "organic-based solution" refers to a solution that is a homogeneous mixture consisting of an organic-based solvent and one or more solutes dissolved in the organic based solvent. An organic-based coating solution refers to an organic-based solution containing at least one polymeric coating material as a solute in the solution.

An "organic-based solvent" is intended to describe a solvent system which consists of one or more organic solvents and about 40% or less, preferably about 30% or less, more preferably about 20% or less, even more preferably about 10% or less, in particular about 5% or less by weight of water relative to the weight of the solvent system.

The invention is generally related to a method for producing, in a consistent manner, SiHy contact lenses each having an intact durable coating thereon, wherein the coating is a hydrogel coating formed by covalently attached a hydrophilic polymeric material onto a base coating of a polyanionic polymer on a SiHy contact lens. This invention is partly based on the discovery that the durability of a hydrogel coating on a SiHy contact lens depends largely upon the processing conditions under which its underlying base coating of polyanionic polymer is formed. When a base coating is applied onto a SiHy contact lens in a single coating step (i.e., by contacting it with one sole coating solution (pH<4.5) of polyanionic polymer for a given coating period of time (e.g., 50 minutes) and followed by one or more rinsing steps, the durability of a hydrogel coating formed on such a base coating can vary with the optical power (i.e., the center thickness) of the SiHy contact lens under coating. For example, the durability of the hydrogel coatings of coated SiHy contact lenses having an optical power of −10.0 diopters is inferior to the durability of the hydrogel coatings of coated SiHy contact lenses having an optical power of −3.0 diopters. A longer coating period could not improve the variation in durability of the hydrogel coating with the optical power (center thickness) of the contact lens. However, it is found that, when the base coating is applied onto a SiHy contact lens by contacting it with one coating solution (having a low pH) of polyanionic polymer even for a shorter coating period of time (e.g., 25 minutes), then rinsing it with a buffered saline having a neutral or slightly basic pH), and then followed by contacting it again with another coating solution (having a low pH) of polyanionic polymer for a shorter period (e.g., 25 minutes), the durability of a hydrogel coating formed on such a base coating can be improved significantly and will not vary with the optical power or the center thickness of the SiHy contact lens under coating.

It is believed that by having adding a step of rinsing with a buffered saline or a solution having a neutral or basic pH between two steps of solution-coating of a polyanionic polymer at a low pH, molecules of the polyanionic polymer, which are loosely bound onto the surface or slightly penetrate into just below the surface, could be removed so as to allow new molecules of polyanionic polymer to penetrate. It also believed that that the added rinsing step would also allow the molecules of polyanionic polymer, which have already partially penetrated inside the silicone hydrogel contact lens, to penetrate further inside and to entangle with the polymer matrix of the silicone hydrogel contact lens during the transition of structural configuration of polyanionic polymer from compact state to extended state when the pH changes from acid to neutral or higher.

The invention provides a method for producing coated SiHy contact lenses each having an intact durable hydrogel coating thereon, the method of invention comprising the steps of: (1) obtaining a preformed SiHy contact lens; (2) forming a base coating on the preformed SiHy contact lens according to a solution-coating procedure to form a treated SiHy contact lens having the base coating thereon, wherein the solution-coating procedure comprises the sub-steps of (a) contacting the preformed SiHy contact lens with a first coating solution for a first coating period of time, wherein the first coating solution has a first pH and comprises from about 0.001% to about 5.0% (preferably from about 0.005% to about 3.0%, more preferably from about 0.01% to about 2.5%, even more preferably from about 0.02% to about 2.0%) by weight of a first polyanionic polymer, (b) rinsing the preformed SiHy contact lens obtained in sub-step (a) with a first buffered saline having a second pH for a first rinsing period of time, (c) optionally rinsing the preformed SiHy contact lens obtained in sub-step (b) with water, one or more organic solvent miscible with water, or a mixture thereof for a second rinsing period of time, (d) contacting the preformed SiHy contact lens obtained in sub-step (b) or (c) with a second coating solution for a second coating period of time, wherein the second coating solution has a third pH and comprises from about 0.001% to about 5.0% (preferably from about 0.005% to about 3.0%, more preferably from about 0.01% to about 2.5%, even more preferably from about 0.02% to about 2.0%) by weight of a second polyanionic polymer, (e) rinsing the preformed SiHy contact lens obtained in sub-step (d) with a second buffered saline having a fourth pH for a third rinsing period of time, (f) optionally rinsing the preformed SiHy contact lens obtained in sub-step (e) with water, one or more organic solvent miscible with water, or a mixture thereof for a fourth rinsing period of time wherein the first and second polyanionic polymer independent of each other are a homo- or copolymer of acrylic acid or $C_1$-$C_3$ alkylacrylic acid, wherein the first pH and the third pH independent of each other are from 0 to about 4.5 (preferably from about 0.5 to about 4.0, more preferably from about 0.5 to about 3.5, even more preferably from about 1.0 to about 3.0), wherein the second pH and the fourth pH independent of each other are from about 6.5 to about 10 (preferably from about 6.8 to about 9.0, more preferably from about 6.8 to about 8.5, even more preferably from about 6.8 to about 8.0); and (3) heating the treated SiHy contact lens having the base coating thereon in an aqueous solution having a pH from about 6.5 to about 9.5 (preferably from about 6.8 to about 9.0, more preferably from about 6.8 to about 8.5, even more preferably from about 6.8 to about 8.0) and including a water-soluble, thermally-crosslinkable hydrophilic polymeric material at a temperature from about 60° C. to about 140° C. to form a coated SiHy contact lens have a hydrogel coating thereon, wherein the hydrogel coating is covalently attached onto the base coating and is intact and durable, wherein the durability of the hydrogel coating is independent of the optical power or the center thickness of the preformed SiHy contact lens. Preferably, the coated SiHy contact lens having the hydrogel coating thereon can pass Sudan Black staining test after being subjected to 30 cycles of digital rubbing treatment or after simulated abrasion cycling treatment.

In accordance with the invention, a preformed SiHy contact lens can be any SiHy contact lens which has not been subjected to any surface treatment after being produced according to any lens manufacturing processes, any SiHy contact lens which has been plasma treated, or any commercial SiHy contact lens, so long as it does not have a water gradient structural configuration.

A person skilled in the art knows very well how to make preformed SiHy contact lenses from a SiHy lens formulation. For example, for production of preformed SiHy (SiHy) contact lenses, a SiHy lens formulation for cast-molding or spin-cast molding or for making SiHy rods used in lathe-cutting of contact lenses generally comprises at least one components selected from the group consisting of a silicone-containing vinylic monomer, a silicone-containing vinylic crosslinker, a silicone-containing prepolymer, a hydrophilic vinylic monomer, a hydrophobic vinylic monomer, a non-silicone vinylic crosslinker, a free-radical initiator (photoinitiator or thermal initiator), a silicone-containing prepolymer, and combination thereof, as well known to a person skilled in the art. Resultant preformed SiHy contact lenses then can be subjected to extraction with an extraction solvent to remove unpolymerized components from the resultant lenses and to hydration process, as known by a person skilled in the art. In addition, a preformed SiHy contact lens can be a colored contact lens (i.e., a SiHy contact lens having at least one colored patterns printed thereon as well known to a person skilled in the art).

In cast-molding, a SiHy lens formulation typically is dispensed into molds and cured (i.e., polymerized and/or crosslinked) in molds for making contact lenses. Lens molds for making contact lenses are well known to a person skilled in the art and, for example, are employed in cast molding or spin casting. For example, a mold (for cast molding) generally comprises at least two mold sections (or portions) or mold halves, i.e. first and second mold halves. The first mold half defines a first molding (or optical) surface and the second mold half defines a second molding (or optical) surface. The first and second mold halves are configured to receive each other such that a lens forming cavity is formed between the first molding surface and the second molding surface. The molding surface of a mold half is the cavity-forming surface of the mold and in direct contact with lens-forming material.

Methods of manufacturing mold sections for cast-molding a contact lens are generally well known to those of ordinary skill in the art. The process of the present invention is not limited to any particular method of forming a mold. In fact, any method of forming a mold can be used in the present invention. The first and second mold halves can be formed through various techniques, such as injection molding or lathing. Examples of suitable processes for forming the mold halves are disclosed in U.S. Pat. Nos. 4,444,711; 4,460,534; 5,843,346; and 5,894,002.

Virtually all materials known in the art for making molds can be used to make molds for making contact lenses. For example, polymeric materials, such as polyethylene, polypropylene, polystyrene, PMMA, Topas® COC grade 8007-S10 (clear amorphous copolymer of ethylene and norbornene, from Ticona GmbH of Frankfurt, Germany and Summit, N.J.), or the like can be used. Other materials that allow UV light transmission could be used, such as quartz glass and sapphire.

In accordance with the invention, the polymerizable composition (i.e., lens formulation) can be introduced (dispensed) into a cavity formed by a mold according to any known methods.

After the polymerizable composition is dispensed into the mold, it is polymerized to produce a contact lens. Cross-linking may be initiated thermally or actinically, preferably by exposing the lens-forming composition in the mold to a spatial limitation of actinic radiation to crosslink the polymerizable components in the polymerizable composition.

Opening of the mold so that the molded article can be removed from the mold may take place in a manner known per se.

The molded SiHy contact lens can be subject to lens extraction to remove unpolymerized polymerizable components. The extraction solvent can be any solvent known to a person skilled in the art. Examples of suitable extraction solvent are those described below.

In accordance with the invention, a silicone-containing vinylic monomer can be any silicone-containing vinylic monomer known to a person skilled in the art. Examples of preferred silicone-containing vinylic monomers include without limitation vinylic monomers each having a bis(trialkylsilyloxy)alkylsilyl group or a tris(trialkylsilyloxy) silyl group, polysiloxane vinylic monomers, polycarbosiloxane vinylic monomer, 3-methacryloxy propylpentamethyldisiloxane, t-butyldimethyl-siloxyethyl vinyl carbonate, trimethylsilylethyl vinyl carbonate, and trimethylsilylmethyl vinyl carbonate, and combinations thereof.

Examples of preferred vinylic monomers each having a bis(trialkylsilyloxy)alkylsilyl group or a tris(trialkylsilyloxy)silyl group include without limitation tris(trimethylsilyloxy)silylpropyl (meth)acrylate, [3-(meth)acryloxy-2-hydroxypropyloxy]propylbis(trimethylsiloxy)methylsilane, [3-(meth)acryloxy-2-hydroxypropyloxy]propylbis(trimethylsiloxy)butylsilane, 3-(meth)acryloxy-2-(2-hydroxyethoxy)-propyloxy)propylbis(trimethylsiloxy)methylsilane, 3-(meth)acryloxy-2-hydroxypropyloxy)propyltris(trimethylsiloxy)silane, N-[tris(trimethylsiloxy)silylpropyl]-(meth)acrylamide, N-(2-hydroxy-3-(3-(bis(trimethylsilyloxy)methysilyl)propyloxy)propyl)-2-methyl (meth)acrylamide, N-(2-hydroxy-3-(3-(bis(trimethylsilyloxy)methylsilyl)propyloxy)propyl) (meth)acrylamide, N-(2-hydroxy-3-(3-(tris(trimethylsilyloxy)silyl)propyloxy)propyl)-2-methyl acrylamide, N-(2-hydroxy-3-(3-(tris(trimethylsilyloxy)silyl) propyloxy)propyl) (meth)acrylamide, N-[tris(dimethylpropylsiloxy)silylpropyl]-(meth)acrylamide, N-[tris(dimethylphenylsiloxy)silylpropyl](meth)acrylamide, N-[tris(dimethylethylsiloxy)silylpropyl] (meth)acrylamide, N,N-bis[2-hydroxy-3-(3-(bis(trimethylsilyloxy) methylsilyl)propyloxy)propyl]-2-methyl (meth)acrylamide, N,N-bis[2-hydroxy-3-(3-(bis(trimethylsilyloxy)methylsilyl) propyloxy)propyl] (meth)acrylamide, N,N-bis[2-hydroxy-3-(3-(tris(trimethylsilyloxy)silyl)propyloxy)propyl]-2-methyl (meth)acrylamide, N,N-bis[2-hydroxy-3-(3-(tris(trimethylsilyloxy)silyl)propyloxy)propyl] (meth)acrylamide, N-[2-hydroxy-3-(3-(t-butyldimethylsilyl)propyloxy)propyl]-2-methyl (meth)acrylamide, N-[2-hydroxy-3-(3-(t-butyldimethylsilyl)propyloxy)propyl] (meth)acrylamide, N,N-bis[2-hydroxy-3-(3-(t-butyldimethylsilyl)propyloxy) propyl]-2-methyl (meth)acrylamide, N-2-(meth)acryloxy-ethyl-O-(methyl-bis-trimethylsiloxy-3-propyl)silyl carbamate, 3-(trimethylsilyl)propylvinyl carbonate, 3-(vinyloxycarbonylthio)propyl-tris(trimethyl-siloxy)silane, 3-[tris(trimethylsiloxy)silyl]propylvinyl carbamate, 3-[tris(trimethylsiloxy)silyl] propyl allyl carbamate, 3-[tris(trimethylsiloxy)silyl]propyl vinyl carbonate, those disclosed in U.S. Pat. Nos. 9,097,840, 9,103,965 and 9,475,827, and mixtures thereof. The above preferred silicone-containing vinylic monomers can be obtained from commercial suppliers or can be prepared according to procedures described in U.S. Pat. Nos. 7,214,809, 8,475,529, 8,658,748, 9,097,840, 9,103,965, and 9,475,827.

Examples of preferred polysiloxane vinylic monomers include without limitation mono-(meth)acryloyl-terminated, monoalkyl-terminated polysiloxanes of formula (I) include without limitation α-(meth)acryloxypropyl terminated ω-butyl (or ω-methyl) terminated polydimethylsiloxane, α-(meth)acryloxy-2-hydroxypropyloxypropyl terminated ω-butyl (or ω-methyl) terminated polydimethylsiloxane, α-(2-hydroxyl-methacryloxypropyloxypropyl)-ω-butyl-decamethylpentasiloxane, α-[3-(meth)acryloxyethoxy-2-hydroxypropyloxypropyl]-terminated ω-butyl (or ω-methyl) terminated polydimethylsiloxane, α-[3-(meth)acryloxy-propyloxy-2-hydroxypropyloxypropyl]-terminated ω-butyl (or ω-methyl) terminated polydimethylsiloxane, α-[3-(meth) acryloxyisopropyloxy-2-hydroxypropyloxypropyl]-terminated ω-butyl (or ω-methyl) terminated polydimethylsiloxane, α-[3-(meth)acryloxybutyloxy-2-hydroxypropyloxypropyl]-terminated ω-butyl (or ω-methyl) terminated polydimethylsiloxane, α-[3-(meth)acryloxyethylamino-2-hydroxypropyloxypropyl]-terminated ω-butyl (or ω-methyl) terminated polydimethylsiloxane, α-[3-(meth)acryloxypropylamino-2-hydroxypropyloxypropyl]-terminated ω-butyl (or ω-methyl) terminated polydimethylsiloxane, α-[3-(meth)acryloxy-butylamino-2-hydroxypropyloxypropyl]-terminated ω-butyl (or ω-methyl) terminated polydimethylsiloxane, α-(meth)acryloxy(polyethylenoxy)-2-hydroxypropyloxypropyl]-terminated ω-butyl (or ω-methyl) terminated polydimethylsiloxane, α-[(meth)acryloxy-2-hydroxypropyloxy-ethoxypropyl]-terminated ω-butyl (or ω-methyl) terminated polydimethylsiloxane, α-[(meth)acryloxy-2-hydroxypropyl-N-ethylaminopropyl]-terminated ω-butyl (or ω-methyl) terminated polydimethylsiloxane, α-[(meth)acryloxy-2-hydroxypropyl-aminopropyl]-terminated ω-butyl (or ω-methyl) terminated polydimethylsiloxane, α-[(meth)acryloxy-2-hydroxypropyloxy-(polyethylenoxy)propyl]-terminated ω-butyl (or ω-methyl) terminated polydimethylsiloxane, α-(meth)acryloylamidopropyloxypropyl terminated ω-butyl (or ω-methyl) terminated polydimethylsiloxane, α-N-methyl-(meth)acryloylamidopropyloxypropyl terminated ω-butyl (or ω-methyl) terminated polydimethylsiloxane, α-[3-(meth)acrylamidoethoxy-2-hydroxypropyloxypropyl]-terminated ω-butyl (or ω-methyl) polydimethylsiloxane, α-[3-(meth)acrylamidopropyloxy-2-hydroxypropyloxypropyl]-terminated ω-butyl (or ω-methyl) terminated polydimethylsiloxane, α-[3-(meth)acrylamidoisopropyloxy-2-hydroxypropyloxypropyl]-terminated ω-butyl (or ω-methyl) terminated polydimethylsiloxane, α-[3-(meth) acrylamidobutyloxy-2-hydroxypropyloxypropyl]-terminated ω-butyl (or ω-methyl) terminated polydimethylsiloxane, α-[3-(meth)acryloylamido-2-hydroxypropyloxypropyl] terminated ω-butyl (or ω-methyl) polydimethylsiloxane, α-[3-[N-methyl-(meth)acryloylamido]-2-hydroxypropyloxypropyl] terminated ω-butyl (or ω-methyl) terminated polydimethylsiloxane, N-methyl-N'-(propyltetra(dimethylsiloxy)dimethylbutylsilane) (meth)acrylamide, N-(2,3-dihydroxypropane)-N'-(propyltetra(dimethylsiloxy)dimethylbutylsilane) (meth)acrylamide, (meth)acryloylamidopropyltetra(dimethylsiloxy)dimethylbutylsilane, monovinyl carbonate-terminated mono-alkyl-terminated polydimethylsiloxanes, monovinyl carbamate-terminated mono-alkyl-terminated polydimethylsiloxane, those disclosed in U.S. Pat. Nos. 9,097,840 and 9,103,965, and mixtures thereof. The above preferred polysiloxanes vinylic monomers can be obtained from commercial suppliers (e.g., Shin-Etsu, Gelest, etc.) or prepared according to procedures described in patents, e.g., U.S. Pat. Nos. 6,867,245, 8,415,405, 8,475,529, 8,614,261, and 9,217,813, or by reacting a hydroxyalkyl (meth)acrylate or (meth)acrylamide or a (meth)acryloxypolyethylene glycol with a mono-epoxypropyloxypropyl-terminated polydimethylsiloxane, by reacting glycidyl (meth)acrylate with a mono-carbinol-terminated polydimethylsiloxane, a mono-aminopropyl-terminated polydimethylsiloxane, or a mono-ethylaminopropyl-terminated polydimethylsiloxane, or by reacting isocyanatoethyl (meth)acrylate with a mono-carbinol-terminated polydimethylsiloxane according to coupling reactions well known to a person skilled in the art.

Any polycarbosiloxane vinylic monomers can be used in the invention. Examples of preferred polycarbosiloxane vinylic monomers include without limitation those disclosed in U.S. Pat. Nos. 7,915,323 and 8,420,711 and in U.S. Pat. Appl. Pub. Nos. 2012/244088A1 and 2012/245249A1.

Any suitable silicone-containing vinylic crosslinkers can be used in the invention. Examples of preferred silicone-containing vinylic crosslinkers include without limitation polysiloxane vinylic crosslinkers, polycarbosiloxane vinylic crosslinkers, and combinations thereof.

Any suitable polysiloxane vinylic crosslinkers can be used in the invention. Examples of preferred polysiloxane vinylic crosslinkers are di-(meth)acryloyl-terminated polydimethylsiloxanes; di-vinyl carbonate-terminated polydimethylsiloxane; di-vinyl carbamate-terminated polydimethylsiloxane; N,N,N',N'-tetrakis(3-methacryloxy-2-hydroxypropyl)-alpha,omega-bis-3-aminopropyl-polydimethylsiloxane; polysiloxane-containing macromer selected from the group consisting of Macromer A, Macromer B, Macromer C, and Macromer D described in U.S. Pat. No. 5,760,100; polysiloxane-containing macromers disclosed in U.S. Pat. Nos. 4,136,250, 4,153,641, 4,182,822, 4,189,546, 4,259,467, 4,260,725, 4,261,875, 4,343,927, 4,254,248, 4,355,147, 4,276,402, 4,327,203, 4,341,889, 4,486,577, 4,543,398, 4,605,712, 4,661,575, 4,684,538, 4,703,097, 4,833,218, 4,837,289, 4,954,586, 4,954,587, 5,010,141, 5,034,461, 5,070,170, 5,079,319, 5,039,761, 5,346,946, 5,358,995, 5,387,632, 5,416,132, 5,451,617, 5,486,579, 5,962,548, 5,981,675, 6,039,913, 6,762,264.

Examples of preferred di-(meth)acryloyloxy-terminated polysiloxane vinylic crosslinkers includes without limitation the reaction products of glycidyl methacrylate with di-amino-terminated polydimethylsiloxanes; the reaction products of glycidyl methacrylate with di-hydroxyl-terminated polydimethylsiloxanes; the reaction products of isocyanatoethyl (meth)acrylate with di-hydroxyl-terminated polydimethylsiloxanes; di-(meth)acryloyloxy-terminated polysiloxane vinylic crosslinkers each having hydrophilized siloxane units each having one methyl substituent and one monovalent $C_4$-$C_{40}$ organic radical substituent having 2 to 6 hydroxyl groups as disclosed in U.S. Pat. No. 10,081,697; chain-extended polysiloxabevinylic crosslinkers disclosed in US201008843A1 and US20120088844A1; chain-extended polysiloxane vinylic crosslinkers described in U.S. Pat. Nos. 5,034,461, 5,416,132, 5,449,729, 5,760,100, 7,423,074, and 8,529,057; chain-extended polysiloxane vinylic crosslinkers described in U.S. Pat. App. Pub. No. 2018-0100053; chain-extended polysiloxane vinylic crosslinkers described in U.S. Pat. App. Pub. No. 2018-0100038; chain-extended polysiloxane vinylic crosslinkers described in U.S. Pat. No. 8,993,651; α,ω-bis[3-(meth)acrylamidopropyl]-terminated polydimethylsiloxane, α,ω-bis[3-(meth)acryloxypropyl]-terminated polydimethylsiloxane, α,ω-bis[3-(meth)acryloxy-2-hydroxypropyloxypropyl]-terminated polydimethylsiloxane, α,ω-bis[3-(meth)acryloxyethoxy-2-hydroxypropyloxypropyl]-terminated polydimethylsiloxane, α,ω-bis[3-(meth)acryloxypropyloxy-2-hydroxypropyloxypropyl]-terminated polydimethylsiloxane, α,ω-bis[3-(meth)acryloxy-isopropyloxy-2-hydroxypropyloxypropyl]-terminated polydimethylsiloxane, α,ω-bis[3-(meth)acryloxybutyloxy-2-hydroxypropyloxypropyl]-terminated polydimethylsiloxane, α,ω-bis[3-(meth)acrylamidoethoxy-2-hydroxypropyloxypropyl]-terminated polydimethylsiloxane, α,ω-bis[3-(meth)acrylamidopropyloxy-2-hydroxypropylpropyl]-terminated polydimethylsiloxane, α,ω-bis[3-(meth)acrylamidoisopropyloxy-2-hydroxypropyloxypropyl]-terminated polydimethylsiloxane, α,ω-bis[3-(meth)acrylamidobutyloxy-2-hydroxypropyloxypropyl]-terminated polydimethylsiloxane, α,ω-bis[3-(meth)acryloxyethylamino-2-hydroxypropyloxypropyl]-terminated polydimethylsiloxane, α,ω-bis[3-(meth)acryloxypropylamino-2-hydroxypropyloxypropyl]-terminated polydimethylsiloxane, α,ω-bis[3-(meth)acryloxybutylamino-2-hydroxypropyloxypropyl]-terminated polydimethylsiloxane, α,ω-bis[(meth)acrylamidoethylamino-2-hydroxypropyloxy-propyl]-terminated polydimethylsiloxane, α,ω-bis[3-(meth)acrylamidopropylamino-2-hydroxypropyloxypropyl]-terminated polydimethylsiloxane, α,ω-bis[3-(meth)acrylamide-butylamino-2-hydroxypropyloxypropyl]-terminated polydimethylsiloxane, α,ω-bis[(meth)acryloxy-2-hydroxypropyloxy-ethoxypropyl]-terminated polydimethylsiloxane, α,ω-bis[(meth)acryloxy-2-hydroxypropyl-N-ethylaminopropyl]-terminated polydimethylsiloxane, α,ω-bis[(meth)acryloxy-2-hydroxypropyl-aminopropyl]-polydimethylsiloxane, α,ω-bis[(meth)acryloxy-2-hydroxypropyloxy-(polyethylenoxy)propyl]-terminated polydimethylsiloxane, α,ω-bis[(meth)acryloxyethylamino-carbonyloxy-ethoxypropyl]-terminated polydimethylsiloxane, α,ω-bis[(meth)acryloxyethylamino-carbonyloxy-(polyethylenoxy)propyl]-terminated polydimethylsiloxane.

Any polycarbosiloxane vinylic crosslinkers can be used in the invention. Examples of preferred polycarbosiloxane vinylic crosslinkers include without limitation those disclosed in U.S. Pat. Nos. 7,915,323, 8,420,711, US2012/0244088A1 and US2012/0245249A1.

Any hydrophilic vinylic monomers can be used in the invention. Examples of preferred hydrophilic vinylic monomers are alkyl (meth)acrylamides (as described below), hydroxyl-containing acrylic monomers (as described below), amino-containing acrylic monomers (as described below), carboxyl-containing acrylic monomers (as described below), N-vinyl amide monomers (as described below), methylene-containing pyrrolidone monomers (i.e., pyrrolidone derivatives each having a methylene group connected to the pyrrolidone ring at 3- or 5-position) (as described below), acrylic monomers having a $C_1$-$C_4$ alkoxyethoxy group (as described below), vinyl ether monomers (as described below), allyl ether monomers (as described below), phosphorylcholine-containing vinylic monomers (as described below), N-2-hydroxyethyl vinyl carbamate, N-carboxyvinyl-β-alanine (VINAL), N-carboxyvinyl-α-alanine, and combinations thereof.

Examples of alkyl (meth)acrylamides includes without limitation (meth)acrylamide, N,N-dimethyl (meth)acrylamide, N-ethyl (meth)acrylamide, N,N-diethyl (meth)acrylamide, N-propyl (meth)acrylamide, N-isopropyl (meth)acrylamide, N-3-methoxypropyl (meth)acrylamide, and combinations thereof.

Examples of hydroxyl-containing acrylic monomers include without limitation N-2-hydroxylethyl (meth)acrylamide, N,N-bis(hydroxyethyl) (meth)acrylamide, N-3-hydroxypropyl (meth)acrylamide, N-2-hydroxypropyl (meth)acrylamide, N-2,3-dihydroxypropyl (meth)acrylamide, N-tris(hydroxymethyl)methyl (meth)acrylamide, 2-hydroxyethyl (meth)acrylate, 3-hydroxypropyl (meth)acrylate, 2-hydroxypropyl (meth)acrylate, glycerol methacrylate (GMA), di(ethylene glycol) (meth)acrylate, tri(ethylene glycol) (meth)acrylate, tetra(ethylene glycol) (meth)acrylate, poly(ethylene glycol) (meth)acrylate having a number average molecular weight of up to 1500, poly(ethylene glycol) ethyl (meth)acrylamide having a number average molecular weight of up to 1500, and combinations thereof.

Examples of amino-containing acrylic monomers include without limitation N-2-aminoethyl (meth)acrylamide, N-2-methylaminoethyl (meth)acrylamide, N-2-ethylaminoethyl (meth)acrylamide, N-2-dimethylaminoethyl (meth)acrylamide, N-3-aminopropyl (meth)acrylamide, N-3-methylaminopropyl (meth)acrylamide, N-3-dimethylaminopropyl (meth)acrylamide, 2-aminoethyl (meth)acrylate, 2-methylaminoethyl (meth)acrylate, 2-ethylaminoethyl (meth)acrylate, 3-aminopropyl (meth)acrylate, 3-methylaminopropyl (meth)acrylate, 3-ethylaminopropyl (meth)acrylate, 3-amino-2-hydroxypropyl (meth)acrylate, trimethylammonium 2-hydroxy propyl (meth)acrylate hydrochloride, dimethylaminoethyl (meth)acrylate, and combinations thereof.

Examples of carboxyl-containing acrylic monomers include without limitation 2-(meth)acrylamidoglycolic acid, (meth)acrylic acid, ethylacrylic acid, and combinations thereof.

Examples of preferred N-vinyl amide monomers include without limitation N-vinylpyrrolidone (aka, N-vinyl-2-pyrrolidone), N-vinyl-3-methyl-2-pyrrolidone, N-vinyl-4-methyl-2-pyrrolidone, N-vinyl-5-methyl-2-pyrrolidone, N-vinyl-6-methyl-2-pyrrolidone, N-vinyl-3-ethyl-2-pyrrolidone, N-vinyl-4,5-dimethyl-2-pyrrolidone, N-vinyl-5,5-dimethyl-2-pyrrolidone, N-vinyl-3,3,5-trimethyl-2-pyrrolidone, N-vinyl piperidone (aka, N-vinyl-2-piperidone), N-vinyl-3-methyl-2-piperidone, N-vinyl-4-methyl-2-piperidone, N-vinyl-5-methyl-2-piperidone, N-vinyl-6-methyl-2-piperidone, N-vinyl-6-ethyl-2-piperidone, N-vinyl-3,5-dimethyl-2-piperidone, N-vinyl-4,4-dimethyl-2-piperidone, N-vinyl caprolactam (aka, N-vinyl-2-caprolactam), N-vinyl-3-methyl-2-caprolactam, N-vinyl-4-methyl-2-caprolactam, N-vinyl-7-methyl-2-caprolactam, N-vinyl-7-ethyl-2-caprolactam, N-vinyl-3,5-dimethyl-2-caprolactam, N-vinyl-4,6-dimethyl-2-caprolactam, N-vinyl-3,5,7-trimethyl-2-caprolactam, N-vinyl-N-methyl acetamide, N-vinyl formamide, N-vinyl acetamide, N-vinyl isopropylamide, N-vinyl-N-ethyl acetamide, N-vinyl-N-ethyl formamide, and mixtures thereof. Preferably, the N-vinyl amide monomer is N-vinylpyrrolidone, N-vinyl-N-methyl acetamide, or combinations thereof.

Examples of preferred methylene-containing ($=CH_2$) pyrrolidone monomers include without limitations 1-methyl-3-methylene-2-pyrrolidone, 1-ethyl-3-methylene-2-pyrrolidone, 1-methyl-5-methylene-2-pyrrolidone, 1-ethyl-5-methylene-2-pyrrolidone, 5-methyl-3-methylene-2-pyrrolidone, 5-ethyl-3-methylene-2-pyrrolidone, 1-n-propyl-3-methylene-2-pyrrolidone, 1-n-propyl-5-methylene-2-pyrrolidone, 1-isopropyl-3-methylene-2-pyrrolidone, 1-isopropyl-5-methylene-2-pyrrolidone, 1-n-butyl-3-methylene-2-pyrrolidone, 1-tert-butyl-3-methylene-2-pyrrolidone, and combinations thereof.

Examples of preferred acrylic monomers having a $C_1$-$C_4$ alkoxyethoxy group include without limitation ethylene glycol methyl ether (meth)acrylate, di(ethylene glycol) methyl ether (meth)acrylate, tri(ethylene glycol) methyl ether (meth)acrylate, tetra(ethylene glycol) methyl ether (meth)acrylate, $C_1$-$C_4$-alkoxy poly(ethylene glycol) (meth)acrylate having a weight average molecular weight of up to 1500, methoxy-poly(ethylene glycol)ethyl (meth)acrylamide having a number average molecular weight of up to 1500, and combinations thereof.

Examples of preferred vinyl ether monomers include without limitation ethylene glycol monovinyl ether, di(ethylene glycol) monovinyl ether, tri(ethylene glycol) monovinyl ether, tetra(ethylene glycol) monovinyl ether, poly(ethylene glycol) monovinyl ether, ethylene glycol methyl vinyl ether, di(ethylene glycol) methyl vinyl ether, tri(ethylene glycol) methyl vinyl ether, tetra(ethylene glycol) methyl vinyl ether, poly(ethylene glycol) methyl vinyl ether, and combinations thereof.

Examples of preferred allyl ether monomers include without limitation allyl alcohol, ethylene glycol monoallyl ether, di(ethylene glycol) monoallyl ether, tri(ethylene glycol) monoallyl ether, tetra(ethylene glycol) monoallyl ether, poly(ethylene glycol) monoallyl ether, ethylene glycol methyl allyl ether, di(ethylene glycol) methyl allyl ether, tri(ethylene glycol) methyl allyl ether, tetra(ethylene glycol) methyl allyl ether, poly(ethylene glycol) methyl allyl ether, and combinations thereof.

Examples of preferred phosphorylcholine-containing vinylic monomers include without limitation (meth)acryloyloxyethyl phosphorylcholine (aka, MPC, or 2-((meth)acryloyloxy)ethyl-2'-(trimethylammonio)ethylphosphate), (meth)acryloyloxypropyl phosphorylcholine (aka, 3-((meth)acryloyloxy)propyl-2'-(trimethylammonio)ethylphosphate), 4-((meth)acryloyloxy)butyl-2'-(trimethylammonio)ethylphosphate, 2-[(meth)acryloylamino]ethyl-2'-(trimethylammonio)-ethylphosphate, 3-[(meth)acryloylamino]propyl-2'-(tnmethylammonio)ethylphosphate, 4-[(meth)acryloylamino]butyl-2'-(trimethylammonio)ethylphosphate, 5-((meth)acryloyloxy)pentyl-2'-(trimethylammonio)ethyl phosphate, 6-((meth)acryloyloxy)hexyl-2'-(trimethylammonio)-ethylphosphate, 2-((meth)acryloyloxy)ethyl-2'-(triethylammonio)ethylphosphate, 2-((meth)acryloyloxy)ethyl-2'-(tripropylammonio)ethylphosphate, 2-((meth)acryloyloxy)ethyl-2'-(tributylammonio)ethyl phosphate, 2-((meth)acryloyloxy)propyl-2'-(trimethylammonio)-ethylphosphate, 2-((meth)acryloyloxy)butyl-2'-(trimethylammonio)ethylphosphate, 2-((meth)acryloyloxy)pentyl-2'-(trimethylammonio)ethylphosphate, 2-((meth)acryloyloxy)hexyl-2'-(trimethylammonio)ethyl phosphate, 2-(vinyloxy)ethyl-2'-(trimethylammonio)ethylphosphate, 2-(allyloxy)ethyl-2'-(trimethylammonio)ethylphosphate, 2-(vinyloxycarbonyl)ethyl-2'-(trimethylammonio)ethyl phosphate, 2-(allyloxycarbonyl)ethyl-2'-(trimethylammonio)-ethylphosphate, 2-(vinylcarbonylamino)ethyl-2'-(trimethylammonio)ethylphosphate, 2-(allyloxycarbonylamino)ethyl-2'-(trimethylammonio)ethyl phosphate, 2-(butenoyloxy)ethyl-2'-(trimethylammonio)ethylphosphate, and combinations thereof.

In accordance with the invention, any hydrophobic vinylic monomers can be in this invention. Examples of preferred hydrophobic vinylic monomers include methyl (meth)acrylate, ethyl (meth)acrylate, propyl (meth)acrylate, isopropyl (meth)acrylate, cyclohexyl (meth)acrylate, 2-ethylhexyl (meth)acrylate, vinyl acetate, vinyl propionate, vinyl butyrate, vinyl valerate, styrene, chloroprene, vinyl chloride, vinylidene chloride, (meth)acrylonitrile, 1-butene, butadiene, vinyl toluene, vinyl ethyl ether, perfluorohexylethyl-thio-carbonyl-aminoethylmethacrylate, isobornyl (meth)acrylate, trifluoroethyl (meth)acrylate, hexafluoro-isopropyl (meth)acrylate, hexafluorobutyl (meth)acrylate, and combinations thereof.

In accordance with the invention, any non-silicone vinylic crosslinkers can be in this invention. Examples of preferred non-silicone vinylic cross-linking agents include without limitation ethyleneglycol di-(meth)acrylate, diethyleneglycol di-(meth)acrylate, triethyleneglycol di-(meth)acrylate, tetraethyleneglycol di-(meth)acrylate, glycerol di-(meth)acrylate, 1,3-propanediol di-(meth)acrylate, 1,3-butanediol di-(meth)acrylate, 1,4-butanediol di-(meth)acrylate, glycerol 1,3-diglycerolate di-(meth)acrylate, ethylenebis[oxy(2-hydroxypropane-1,3-diyl)] di-(meth)acrylate, bis[2-(meth)acryloxyethyl] phosphate, trimethylolpropane di-(meth)acrylate, and 3,4-bis[(meth)acryloyl]tetrahydrofuan, diacrylamide, dimethacrylamide, N,N-di(meth)acryloyl-N-methylamine, N,N-di(meth)acryloyl-N-ethylamine, N,N'-methylene bis(meth)acrylamide, N,N'-ethylene bis(meth)acrylamide, N,N'-dihydroxyethylene bis(meth)acrylamide, N,N'-propylene bis(meth)acrylamide, N,N'-2-hydroxypropylene bis(meth)acrylamide, N,N'-2,3-dihydroxybutylene bis(meth)acrylamide, 1,3-bis(meth)acrylamidepropane-2-yl dihydrogen phosphate, piperazine diacrylamide, tetraethyleneglycol divinyl ether, triethyleneglycol divinyl ether, diethyleneglycol divinyl ether, ethyleneglycol divinyl ether, triallyl isocyanurate, triallyl cyanurate, trimethylopropane trimethacrylate, pentaerythritol tetramethacrylate, bisphenol A dimethacrylate, allylmethacrylate, allylacrylate, N-allyl-methacrylamide, N-allyl-acrylamide, and combinations thereof. A preferred non-silicone vinylic cross-linking agent is tetra(ethyleneglycol) di-(meth)acrylate, tri(ethyleneglycol) di-(meth)acrylate, ethyleneglycol di-(meth)acrylate, di(ethyleneglycol) di-(meth)acrylate, tetraethyleneglycol divinyl ether, triethyleneglycol divinyl ether, diethyleneglycol divinyl ether, ethyleneglycol divinyl ether, triallyl isocyanurate, triallyl cyanurate, and combinations thereof.

Any thermal polymerization initiators can be used in the invention. Suitable thermal polymerization initiators are known to the skilled artisan and comprise, for example peroxides, hydroperoxides, azo-bis(alkyl- or cycloalkylnitriles), persulfates, percarbonates, or mixtures thereof. Examples of preferred thermal polymerization initiators include without limitation benzoyl peroxide, t-butyl peroxide, t-amyl peroxybenzoate, 2,2-bis(tert-butylperoxy)butane, 1,1-bis(tert-butylperoxy)cyclohexane, 2,5-Bis(tert-butylperoxy)-2,5-dimethylhexane, 2,5-bis(tert-butylperoxy)-2,5-dimethyl-3-hexyne, bis(1-(tert-butylperoxy)-1-methylethyl)benzene, 1,1-bis(tert-butylperoxy)-3,3,5-trimethylcyclohexane, di-t-butyl-diperoxyphthalate, t-butyl hydro-peroxide, t-butyl peracetate, t-butyl peroxybenzoate, t-butylperoxy isopropyl carbonate, acetyl peroxide, lauroyl peroxide, decanoyl peroxide, dicetyl peroxydicarbonate, di(4-t-butylcyclohexyl) peroxy dicarbonate (Perkadox 16S), di(2-ethylhexyl)peroxy dicarbonate, t-butylperoxy pivalate (Lupersol 11); t-butylperoxy-2-ethylhexanoate (Trigonox 21-C50), 2,4-pentanedione peroxide, dicumyl peroxide, peracetic acid, potassium persulfate, sodium persulfate, ammonium persulfate, 2,2'-azobis(4-methoxy-2,4-dimethylvaleronitile) (VAZO 33), 2,2'-Azobis[2-(2-imidazolin-2-yl)propane]dihydrochloride (VAZO 44), 2,2'-azobis(2-amidinopropane) dihydrochloride (VAZO 50), 2,2'-azobis(2,4-dimethylvaleronitrile) (VAZO 52), 2,2'-azobis(isobutyronitrile) (VAZO 64 or AIBN), 2,2'-azobis-2-methylbutyronitrile (VAZO 67), 1,1-azobis(1-cyclohexanecarbonitrile) (VAZO 88); 2,2'-azobis (2-cyclopropylpropionitrile), 2,2'-azobis(methylisobutyrate), 4,4'-Azobis(4-cyanovaleric acid), and combinations thereof. Preferably, the thermal initiator is 2,2'-azobis(isobutyronitrile) (AIBN or VAZO 64).

Suitable photoinitiators are benzoin methyl ether, diethoxyacetophenone, a benzoylphosphine oxide, 1-hydroxycyclohexyl phenyl ketone and Darocur and Irgacur types, preferably Darocur 1173®) and Darocur 2959®), Germanium-based Norrish Type I photoinitiators (e.g., those described in U.S. Pat. No. 7,605,190). Examples of benzoylphosphine initiators include 2,4,6-trimethylbenzoyldiphenylophosphine oxide; bis-(2,6-dichlorobenzoyl)-4-N-propylphenylphosphine oxide; and bis-(2,6-dichlorobenzoyl)-4-N-butylphenylphosphine oxide.

Reactive photoinitiators which can be incorporated, for example, into a macromer or can be used as a special monomer are also suitable. Examples of reactive photoinitiators are those disclosed in EP 632 329.

Any silicone-containing prepolymers comprising hydrophilic segments and hydrophobic segments can be used in the invention. Examples of such silicone-containing prepolymers include those described in U.S. Pat. Nos. 6,039,913, 7,091,283, 7,268,189, 7,238,750, 7,521,519, 8,383,744, and 8,642,712; and U.S. Pat. Appl. Pub. Nos. 2008/0015315A1, 2008/0143958A1, 2008/0143003A1, 2008/0234457A1, 2008/0231798A1.

A SiHy contact lens formulation can also comprise other necessary components known to a person skilled in the art, such as, for example, a UV-absorbing vinylic monomer, a HEVL-absorbing vinylic monomer, a visibility tinting agent (e.g., reactive dyes, polymerizable dyes, pigments, or mixtures thereof, as well known to a person skilled in the art), antimicrobial agents (e.g., preferably silver nanoparticles), a bioactive agent, leachable lubricants, leachable tear-stabilizing agents, and mixtures thereof, as known to a person skilled in the art.

In accordance with a preferred embodiment of the invention, a preformed SiHy contact lens of the invention can further comprise (but preferably comprises) repeating units of one or more UV-absorbing vinylic monomers and optionally (but preferably) one or more UV/HEVL-absorbing vinylic monomers. The term "UV/HEVL-absorbing vinylic monomer" refers to a vinylic monomer that can absorb UV light and high-energy-violet-light (i.e., light having wavelength between 380 nm and 440 nm.

Any suitable UV-absorbing vinylic monomers and UV/HEVL-absorbing vinylic monomers can be used in a polymerizable composition for preparing a preformed SiHy contact lens of the invention. Examples of preferred UV-absorbing and UV/HEVL-absorbing vinylic monomers include without limitation: 2-(2-hydroxy-5-vinylphenyl)-2H-benzotriazole, 2-(2-hydroxy-5-acrylyloxyphenyl)-2H-benzotriazole, 2-(2-hydroxy-3-methacrylamido methyl-5- tert octylphenyl) benzotriazole, 2-(2'-hydroxy-5'-methacrylamidophenyl)-5-chlorobenzotriazole, 2-(2'-hydroxy-5'-methacrylamidophenyl)-5-methoxybenzotriazole, 2-(2'-hydroxy-5'-methacryloxypropyl-3'-t-butyl-phenyl)-5-chlorobenzotriazole, 2-(2'-hydroxy-5'-methacryloxypropylphenyl) benzotriazole, 2-hydroxy-5-methoxy-3-(5-(trifluoromethyl)-2H-benzo[d][1,2,3]triazol-2-yl)benzyl methacrylate (WL-1), 2-hydroxy-5-methoxy-3-(5-methoxy-2H-benzo[d][1,2,3]triazol-2-yl)benzyl methacrylate (WL-5), 3-(5-fluoro-2H-benzo[d][1,2,3]triazol-2-yl)-2-hydroxy-5-methoxybenzyl methacrylate (WL-2), 3-(2H-benzo[d][1,2,3]triazol-2-yl)-2-hydroxy-5-methoxybenzyl methacrylate (WL-3), 3-(5-chloro-2H-benzo[d][1,2,3]triazol-2-yl)-2-hydroxy-5-methoxybenzyl methacrylate (WL-4), 2-hydroxy-5-methoxy-3-(5-methyl-2H-benzo[d][1,2,3]triazol-2-yl)benzyl methacrylate (WL-6), 2-hydroxy-5-methyl-3-(5-(trifluoromethyl)-2H-benzo[d][1,2,3]triazol-2-yl)benzyl methacrylate (WL-7), 4-allyl-2-(5-chloro-2H-benzo[d][1,2,3]triazol-2-yl)-6-methoxyphenol (WL-8), 2-{2'-Hydroxy-3'-tert-5'[3"-(4"-vinylbenzyloxy)propoxy]phenyl}-5-methoxy-2H-benzotriazole, phenol, 2-(5-chloro-2H-benzotriazol-2-yl)-6-(1,1-dimethylethyl)-4-ethenyl-(UVAM), 2-[2'-hydroxy-5'-(2-methacryloxyethyl)phenyl)]-2H-benzotriazole (2-Propenoic acid, 2-methyl-, 2-[3-(2H-benzotriazol-2-yl)-4-hydroxyphenyl]ethyl ester, Norbloc), 2-{2'-Hydroxy-3'-tert-butyl-5'-[3'-methacryloyloxypropoxy]phenyl}-2H-benzotriazole, 2-{2'-Hydroxy-3'-tert-butyl-5'-[3'-methacryloyloxypropoxy]phenyl}-5-methoxy-2H-benzotriazole (UV13), 2-{2'-Hydroxy-3'-tert-butyl-5'-[3'-methacryloyloxypropoxy]phenyl}-5-chloro-2H-benzotriazole (UV28), 2-[2'-Hydroxy-3'-tert-butyl-5'-(3'-acryloyloxypropoxy)phenyl]-5-trifluoromethyl-2H-benzotriazole (UV23), 2-(2'-hydroxy-5-methacrylamidophenyl)-5-methoxybenzotriazole (UV6), 2-(3-allyl-2-hydroxy-5-methylphenyl)-2H-benzotriazole (UV9), 2-(2-Hydroxy-3-methallyl-5-methylphenyl)-2H-benzotriazole (UV12), 2-3'-t-butyl-2'-hydroxy-5'-(3"-dimethylvinylsilylpropoxy)-2'-hydroxy-phenyl)-5-methoxybenzotriazole (UV15), 2-(2'-hydroxy-5'-methacryloylpropyl-3'-tert-butyl-phenyl)-5-methoxy-2H-benzotriazole (UV16), 2-(2'-hydroxy-5'-acryloylpropyl-3'-tert-butyl-phenyl)-5-methoxy-2H-benzotriazole (UV16A), 2-Methylacrylic acid 3-[3-tert-butyl-5-(5-chlorobenzotriazol-2-yl)-4-hydroxyphenyl]-propyl ester (16-100, CAS #96478-15-8), 2-(3-(tert-butyl)-4-hydroxy-5-(5-methoxy-2H-benzo[d][1,2,3]triazol-2-yl)phenoxy)ethyl methacrylate (16-102); Phenol, 2-(5-chloro-2H-benzotriazol-2-yl)-6-methoxy-4-(2-propen-1-yl) (CAS #1260141-20-5); 2-[2-Hydroxy-5-[3-(methacryloyloxy)propyl]-3-tert-butylphenyl]-5-chloro-2H-benzotriazole; Phenol, 2-(5-ethenyl-2H-benzotriazol-2-yl)-4-methyl-, homopolymer (9Cl) (CAS #83063-87-0). In accordance with the invention, the polymerizable composition comprises about 0.1% to about 3.0%, preferably about 0.2% to about 2.5%, more preferably about 0.3% to about 2.0%, by weight of one or more UV-absorbing vinylic monomers, related to the amount of all polymerizable components in the polymerizable composition.

Where a vinylic monomer capable of absorbing ultraviolet radiation and high energy violet light (HEVL) is used in the invention, a Germane-based Norrish Type I photoinitiator and a light source including a light in the region of about 400 to about 550 nm are preferably used to initiate a free-radical polymerization. Any Germane-based Norrish Type I photoinitiators can be used in this invention, so long as they are capable of initiating a free-radical polymerization under irradiation with a light source including a light in the region of about 400 to about 550 nm. Examples of Germane-based Norrish Type I photoinitiators are acylgermanium compounds described in U.S. Pat. No. 7,605,190.

The bioactive agent is any compound that can prevent a malady in the eye or reduce the symptoms of an eye malady. The bioactive agent can be a drug, an amino acid (e.g., taurine, glycine, etc.), a polypeptide, a protein, a nucleic acid, or any combination thereof. Examples of drugs useful herein include, but are not limited to, rebamipide, ketotifen, olaptidine, cromoglycolate, cyclosporine, nedocromil, levocabastine, lodoxamide, ketotifen, or the pharmaceutically acceptable salt or ester thereof. Other examples of bioactive agents include 2-pyrrolidone-5-carboxylic acid (PCA), alpha hydroxyl acids (e.g., glycolic, lactic, malic, tartaric, mandelic and citric acids and salts thereof, etc.), linoleic and gamma linoleic acids, and vitamins (e.g., B5, A, B6, etc.).

Examples of leachable lubricants include without limitation mucin-like materials (e.g., polyglycolic acid) and non-crosslinkable hydrophilic polymers (i.e., without ethylenically unsaturated groups). Any hydrophilic polymers or copolymers without any ethylenically unsaturated groups can be used as leachable lubricants. Preferred examples of non-crosslinkable hydrophilic polymers include, but are not limited to, polyvinyl alcohols (PVAs), polyamides, polyimides, polylactone, a homopolymer of a vinyl lactam, a copolymer of at least one vinyl lactam in the presence or in the absence of one or more hydrophilic vinylic comonomers, a homopolymer of acrylamide or methacrylamide, a copolymer of acrylamide or methacrylamide with one or more hydrophilic vinylic monomers, polyethylene oxide (i.e., polyethylene glycol (PEG)), a polyoxyethylene derivative, poly-N—N-dimethylacrylamide, polyacrylic acid, poly 2 ethyl oxazoline, heparin polysaccharides, polysaccharides, and mixtures thereof. The number average molecular weight $M_n$ of the non-crosslinkable hydrophilic polymer is preferably from 5,000 to 1,000,000.

Examples of leachable tear-stabilizing agents include, without limitation, phospholipids, monoglycerides, diglycerides, triglycerides, glycolipids, glyceroglycolipids, sphingolipids, sphingo-glycolipids, fatty alcohols, fatty acids, mineral oils, and mixtures thereof. Preferably, a tear stabilizing agent is a phospholipid, a monoglyceride, a diglyceride, a triglyceride, a glycolipid, a glyceroglycolipid, a sphingolipid, a sphingo-glycolipid, a fatty acid having 8 to 36 carbon atoms, a fatty alcohol having 8 to 36 carbon atoms, or a mixture thereof.

A polymerizable composition (SiHy lens formulation) can be a solventless clear liquid prepared by mixing all polymerizable components and other necessary component or a solution prepared by dissolving all of the desirable components in any suitable solvent, such as, a mixture of water and one or more organic solvents miscible with water, an organic solvent, or a mixture of one or more organic solvents, as known to a person skilled in the art. The term "solvent" refers to a chemical that cannot participate in free-radical polymerization reaction.

A solventless lens SiHy lens formulation typically comprises at least one blending vinylic monomer as a reactive solvent for dissolving all other polymerizable components of the solventless SiHy lens formulation. Examples of preferred blending vinylic monomers include $C_1$-$C_{10}$ alkyl (meth)acrylate (e.g., methyl (meth)acrylate, ethyl (meth)acrylate, propyl (meth)acrylate, isopropyl (meth)acrylate, 2-ethylhexyl (meth)acrylate, pentyl (meth)acrylate, hexyl (meth)acrylate, etc.), cyclopentylacrylate, cyclohexylmethacrylate, cyclohexylacrylate, isobornyl (meth)acrylate, styrene, 4,6-trimethylstyrene (TMS), t-butyl styrene (TBS), trifluoroethyl (meth)acrylate, hexafluoro-isopropyl (meth) acrylate, hexafluorobutyl (meth)acrylate, or combinations thereof. Preferably, methyl methacrylate is used as a blending vinylic monomer in preparing a solventless SiHy lens formulation.

Any solvents can be used in the invention. Example of preferred organic solvents includes without limitation, tetrahydrofuran, tripropylene glycol methyl ether, dipropylene glycol methyl ether, ethylene glycol n-butyl ether, ketones (e.g., acetone, methyl ethyl ketone, etc.), diethylene glycol n-butyl ether, diethylene glycol methyl ether, ethylene glycol phenyl ether, propylene glycol methyl ether, propylene glycol methyl ether acetate, dipropylene glycol methyl ether acetate, propylene glycol n-propyl ether, dipropylene glycol n-propyl ether, tripropylene glycol n-butyl ether, propylene glycol n-butyl ether, dipropylene glycol n-butyl ether, tripropylene glycol n-butyl ether, propylene glycol phenyl ether dipropylene glycol dimethyl ether, polyethylene glycols, polypropylene glycols, ethyl acetate, butyl acetate, amyl acetate, methyl lactate, ethyl lactate, i-propyl lactate, methylene chloride, 2-butanol, 1-propanol, 2-propanol, menthol, cyclohexanol, cyclopentanol and exonorborneol, 2-pentanol, 3-pentanol, 2-hexanol, 3-hexanol, 3-methyl-2-butanol, 2-heptanol, 2-octanol, 2-nonanol, 2-decanol, 3-octanol, norborneol, tert-butanol, tert-amyl alcohol, 2-methyl-2-pentanol, 2,3-dimethyl-2-butanol, 3-methyl-3-pentanol, 1-methylcyclohexanol, 2-methyl-2-hexanol, 3,7-dimethyl-3-octanol, 1-chloro-2-methyl-2-propanol, 2-methyl-2-heptanol, 2-methyl-2-octanol, 2-2-methyl-2-nonanol, 2-methyl-2-decanol, 3-methyl-3-hexanol, 3-methyl-3-heptanol, 4-methyl-4-heptanol, 3-methyl-3-octanol, 4-methyl-4-octanol, 3-methyl-3-nonanol, 4-methyl-4-nonanol, 3-methyl-3-octanol, 3-ethyl-3-hexanol, 3-methyl-3-heptanol, 4-ethyl-4-heptanol, 4-propyl-4-heptanol, 4-isopropyl-4-heptanol, 2,4-dimethyl-2-pentanol, 1-methylcyclopentanol, 1-ethylcyclopentanol, 1-ethylcyclopentanol, 3-hydroxy-3-methyl-1-butene, 4-hydroxy-4-methyl-1-cyclopentanol, 2-phenyl-2-propanol, 2-methoxy-2-methyl-2-propanol 2,3,4-trimethyl-3-pentanol, 3,7-dimethyl-3-octanol, 2-phenyl-2-butanol, 2-methyl-1-phenyl-2-propanol and 3-ethyl-3-pentanol, 1-ethoxy-2-propanol, 1-methyl-2-propanol, t-amyl alcohol, isopropanol, 1-methyl-2-pyrrolidone, N,N-dimethylpropionamide, dimethyl formamide, dimethyl acetamide, dimethyl propionamide, N-methyl pyrrolidinone, and mixtures thereof.

Numerous SiHy lens formulations have been described in numerous patents and patent applications published by the filing date of this application and have been used in producing commercial SiHy contact lenses. Examples of commercial SiHy contact lenses include, without limitation, asmofilcon A, balafilcon A, comfilcon A, delefilcon A, efrofilcon A, enfilcon A, fanfilcon A, galyfilcon A, lotrafilcon A, lotrafilcon B, narafilcon A, narafilcon B, senofilcon A, senofilcon B, senofilcon C, smafilcon A, somofilcon A, and stenfilcon A.

A SiHy lens formulation (i.e., polymerizable composition) can be cured (polymerized) thermally or actinically as known to a person skilled in the art, preferably in molds for cast molding of contact lenses.

The thermal polymerization is carried out conveniently, for example at a temperature of from 25 to 120° C. and preferably 40 to 100° C. The reaction time may vary within wide limits, but is conveniently, for example, from 1 to 24 hours or preferably from 2 to 12 hours. It is advantageous to previously degas the components and solvents used in the polymerization reaction and to carry out said copolymerization reaction under an inert atmosphere, for example under a nitrogen or argon atmosphere.

The actinic polymerization can then be triggered off by actinic radiation, for example light, in particular UV light or visible light of a suitable wavelength. The spectral requirements can be controlled accordingly, if appropriate, by addition of suitable photosensitizers.

In a preferred embodiment, the preformed contact lens comprises a SiHy bulk material which comprises: (1) repeating units of at least one polysiloxane vinylic monomer (preferably selected from those described above); (2) repeating units of at least one hydrophilic vinylic monomer (preferably selected from those described above); (3) repeating units of at least one polysiloxane vinylic crosslinker (preferably selected from those described above); (4) repeating units of at least one hydrophilic N-vinyl amide monomer (preferably selected from those described above); (5) repeating units of at least one polycarbosiloxane vinylic monomer (preferably selected from those described above); (6) repeating units of at least one polycarbosiloxane vinylic crosslinker (preferably selected from those described above); (7) repeating units of at least one silicone-containing vinylic monomer having a bis(trialkylsilyloxy)alkylsilyl or tris(trialkylsilyloxy)silyl group (preferably selected from those described above); (8) repeating units of one or more blending vinylic monomers (preferably selected from those described above); (9) repeating units of one or more non-silicone vinylic crosslinking agents (preferably selected from those described above); or (10) combinations thereof.

In a preferred embodiment, the preformed contact lens is a commercial SiHy contact lens (any one described above).

In accordance with the invention, the preformed SiHy contact lens has an oxygen permeability of at least about 50, preferably at least about 60, more preferably at least about 70, even more preferably at least about 90 barrers, most preferably at least about 110 Barrers. The preformed SiHy contact lens can also have an equilibrium water content of from about 10% to about 70%, preferably from about 35% to about 70%, more preferably from about 40% to about 65%; even more preferably from about 40% to about 60%, most preferably from about 40% to about 55% by weight.

In accordance any one of the preferred embodiments of the invention, the preformed SiHy contact lens is naturally wettable without being subjected to any post-curing surface treatment. Naturally-wettable preformed SiHy contact lenses are disclosed in U.S. Pat. Nos. 6,367,929, 6,822,016, 7,052,131, 7,249,848, 6,867,245, 7,268,198, 7,540,609, 7,572,841, 7,750,079, 7,934,830, 8,231,218, 8,367,746, 8,445,614, 8,481,662, 8,487,058, 8,513,325, 8,703,891, 8,820,928, 8,865,789, 8,937,110, 8,937,111, 9,057,821, 9,057,822, 9,121,998, 9,125,808, 9,140,825, 9,140,908, 9,156,934, 9,164,298, 9,170,349, 9,188,702, 9,217,813, 9,296,159, 9,322,959, 9,322,960, 9,360,594, and 9,529,119; and in U.S. patent application Ser. Nos. 16/000,930 and 16/000,933.

A method of the invention is particularly useful for applying a durable hydrogel coating onto a preformed silicone hydrogel contact lens which has an equilibrium water content of about 35% to about 70% (preferably about 40% to about 65%) by weight. It is believed that such a preformed silicone hydrogel contact lens may have relatively large pore size within the silicone hydrogel material and may have relatively higher difficulty in forming a durable hydrogel coating in a consistent manner. A naturally-wettable preformed contact lens having a relatively high equilibrium water content may have an even higher difficulty in forming a durable hydrogel coating in a consistent manner.

The preformed SiHy contact lens can further have a bulk elastic modulus or bulk Young Modulus (hereinafter the terms, "softness," "elastic modulus," and "Young's modulus," are interchangeably used in this application to mean bulk elastic modulus if the term is not modified by the word "surface.") of from about 0.3 MPa to about 1.8 MPa, preferably from 0.4 MPa to about 1.5 MPa, more preferably from about 0.5 MPa to about 1.2 MPa. A person skilled in the art knows well how to determine the elastic modulus and water content of a SiHy material or a SiHy contact lens. For example, all commercial SiHy contact lenses have reported values of oxygen permeability, elastic modulus and water content.

In accordance with the invention, contacting of a preformed SiHy contact lens with any coating solution of a polyanionic polymer can occur by dipping it into the coating solution or by spraying it with the coating solution. One contacting process involves solely dipping the preformed SiHy contact lens in a bath of a coating solution for a period of time or alternatively dipping the preformed SiHy contact lens sequentially in a series of bath of coating solutions for a fixed shorter time period for each bath. Another contacting process involves solely spray a coating solution. However, a number of alternatives involve various combinations of spraying- and dipping-steps may be designed by a person having ordinary skill in the art.

Any polyanionic polymers (i.e., a polymeric having multiple anionic groups at a neutral pH) can be used in forming a base coating on a preformed SiHy contact lens. In accordance with the invention, a polyanionic polymer used in a method of the invention is a homo- or copolymer of acrylic acid, $C_1$-$C_3$ alkylacrylic acid (i.e., methacrylic acid, ethylacrylic acid, propylacrylic acid) or a mixture thereof. Examples of preferred polyanionic polymers include without limitations polyacrylic acid, polymethacrylic acid, poly (ethylacrylic acid), poly(propyacrylic acid), poly(acrylic acid-co-methacrylic acid), poly(acrylic acid-co-ethylacrylic acid), poly(acrylic acid-co-propylacrylic acid), poly[ethylacrylic acid-co-(meth)acrylic acid], poly[propylacrylic acid-co-(meth)acrylic acid], poly[ethylacrylic acid-co-propylacrylic acid], and mixtures thereof. Preferably, a polyanionic polymer is polyacrylic acid, polymethacrylic acid, poly(acrylic acid-co-methacrylic acid), or a mixture thereof.

In accordance with the invention, the weight average molecular weight $M_w$ of a polyanionic polymer for forming a base coating on preformed SiHy contact lenses is from about 50,000 to about 10,000,000 Daltons, preferably from about 100,000 to about 5,000,000 Daltons, more preferably from about 200,000 Daltons to about 2,000,000 Daltons.

Any coating solution of any polyanionic polymer used in a solution-coating procedure for forming a base coating on preformed SiHy contact lenses can be prepared by dissolving one or more polyanionic polymers in water, a mixture of water and one or more organic solvents miscible with water, an organic solvent, or a mixture of one or more organic solvent. Preferably, the polyanionic polymer is dissolved in a mixture of water and one or more organic solvents, an organic solvent, or a mixture of one or more organic solvent. It is believed that a solvent system containing at least one organic solvent can swell a preformed SiHy contact lens so that a portion of the polyanionic polymer may penetrate into the preformed SiHy contact lens and increase the durability and thickness of the base coating. Any organic solvents described above can be used in preparation of a solution of the polyanionic polymer, so long as it can dissolve the polyanionic polymer.

The concentration of polyanionic polymer is from about 0.001% to about 5.0%, preferably from about 0.005% to about 3.0%, more preferably from about 0.01% to about 2.5%, even more preferably from about 0.02% to about 2.0% by weight relative to the total weight of the solution.

As known to a person skilled in the art, the thickness of the base coating can be adjusted by varying the concentration of the polyanionic polymer, the contacting time of the preformed contact lens with the solution of the polyanionic polymer, the solvent system (e.g., the amount of one or more organic solvents), pH or ionic strength of the solution, or combinations thereof.

In accordance with the invention, the pH of any coating solutions (including the first and second coating solutions) used in the solution-coating procedure is from 0 to about 4.5, preferably from about 0.5 to about 4.0, more preferably from about 0.5 to about 3.5, even more preferably from about 1.0 to about 3.0. Such a pH can be achieved in by adding any inorganic or organic acid, preferably sulfuric acid or formic acid, more preferably formic acid, into the coating solution. It is understood that homo- or copolymers of acrylic acid or C2-C3 alkylacrylic acid are presented in fully-protonated form in a solution having such a pH and may easily penetrate partially into a preformed SiHy contact lens.

In accordance with the invention, any buffered saline or solution can be used as one of the rinsing solutions in the solution-coating procedure, so long as it has a pH from about 6.5 to about 10 (preferably from about 6.8 to about 9.0, more preferably from about 6.8 to about 8.5, even more preferably from about 6.8 to about 8.0). Preferably, a phosphate-buffered or bicarbonate-buffered saline is used as a rinsing solution.

In accordance with the invention, the thermally-crosslinkable hydrophilic polymeric material for forming the outer surface hydrogel layer (i.e., the crosslinked hydrophilic coating) comprises crosslinkable groups, preferably thermally-crosslinkable groups (e.g., epoxy groups, azetidinium groups, or combinations thereof), more preferably azetidinium groups. Preferably, the water-soluble and crosslinkable hydrophilic polymeric material is a partially-crosslinked polymeric material that comprises a three-dimensional network and preferably thermally-crosslinkable groups, more preferably azetidinium groups within the network or being attached to the network. The term "partially-crosslinked" in reference to a polymeric material means that the crosslinkable groups of starting materials for making the polymeric material in crosslinking reaction have not been fully consumed. For example, such a thermally-crosslinkable hydrophilic polymeric material comprises azetidinium groups and is a partial reaction product of at least one azetidinium-containing polymer with at least one hydrophilicity-enhancing agent (i.e., a wetting agent) having at least one carboxyl, primary amine, secondary amine, or thiol group, according to the crosslinking reactions shown in Scheme I Scheme I

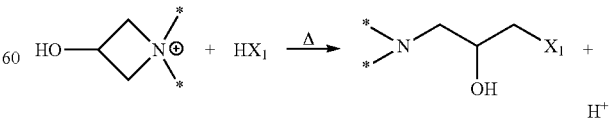

in which $X_1$ is —S—*, —OC(=O)—*, or —NR'—* in which R' is hydrogen or a $C_1$-$C_{20}$ unsubstituted or substituted alkyl group, and * represents an organic radical.

Any suitable azetidinium-containing polymers can be used in the invention. Examples of azetidinium-containing polymers includes without limitation epichlorohydrin-functionalized polyamines, homopolymers of an azetidinium-containing vinylic monomer, copolymers of an azetidinium-containing vinylic monomer with one or more vinylic monomers.

Preferably, an azetidinium-containing polymer is an epichlorohydrin-functionalized polyamine. An epichlorohydrin-functionalized polyamine can be obtained by reacting epichlorohydrin with a polyamine polymer or a polymer containing secondary amino groups. For example, a poly(alkylene imines) or a poly(amidoamine) which is a polycondensate derived from a polyamine and a dicarboxylic acid (e.g., adipic acid-diethylenetriamine copolymers) can react with epichlorohydrin to form an epichlorohydrin-functionalized polymer; a homopolymer or copolymer of mono-alkylaminoalkyl (meth)acrylate or mono-alkylaminoalkyl (meth)acrylamide can also react with epichlorohydrin to form an epichlorohydrin-functionalized polyamine; a poly(2-oxazoline-co-ethyleneimine) copolymer can react with epichlorohydrin to form an epichlorohydrin-functionalized polyamine (i.e., a poly(2-oxazoline-co-ethyleneimine)-epichlorohydrin). The reaction conditions for epichlorohydrin-functionalization of a polyamine or polyamidoamine polymer are taught in EP1465931. A preferred epichlorohydrin-functionalized polyamine is polyamidoamine-epichlorohydrin (PAE) or a poly(2-oxazoline-co-ethyleneimine)-epichlorohydrin.

Polyamidoamine-epichlorohydrin is commercially available, such as, for example, Kymene® or Polycup® resins (epichlorohydrin-functionalized adipic acid-diethylenetriamine copolymers) from Hercules.

Poly(2-oxazoline-co-ethyleneimine)-epichlorohydrin can be prepared according to procedures described in U.S. Pat. Appl. Pub. No. US 2016/0061995 A1.

Homopolymers and copolymers of an azetidinium-containing vinylic monomer can be obtained according to the procedures described in U.S. Pat. Appl. Pub. No. 2013/0337160A1.

Any suitable hydrophilicity-enhancing agents can be used in the invention so long as they are ophthalmically compatible and contain at least one amino group, at least one carboxyl group, and/or at least one thiol group, preferably contain at least one carboxyl group, at least one thiol group, or combinations thereof.

A preferred class of hydrophilicity-enhancing agents include without limitation: primary amino-, secondary amino-, carboxyl- or thiol-containing monosaccharides (e.g., 3-amino-1,2-propanediol, 1-thiolglycerol, 5-keto-D-gluconic acid, galactosamine, glucosamine, galacturonic acid, gluconic acid, glucosaminic acid, mannosamine, saccharic acid 1,4-lactone, saccharide acid, Ketodeoxynonulosonic acid, N-methyl-D-glucamine, 1-amino-1-deoxy-β-D-galactose, 1-amino-1-deoxysorbitol, 1-methylamino-1-deoxysorbitol, N-aminoethyl gluconamide); primary amino-, secondary amino-, carboxyl- or thiol-containing disaccharides (e.g., chondroitin disaccharide sodium salt, di(β-D-xylopyranosyl)amine, digalacturonic acid, heparin disaccharide, hyaluronic acid disaccharide, Lactobionic acid); and primary amino-, secondary amino-, carboxyl- or thiol-containing oligosaccharides (e.g., carboxymethyl-β-cyclodextrin sodium salt, trigalacturonic acid); and combinations thereof.

Another preferred class of hydrophilicity-enhancing agents is hydrophilic polymers having one or more (primary or secondary) amino, carboxyl and/or thiol groups. More preferably, the content of the amino (—NHR' with R' as defined above), carboxyl (—COOH) and/or thiol (—SH) groups in a hydrophilic polymer as a hydrophilicity-enhancing agent is less than about 40%, preferably less than about 30%, more preferably less than about 20%, even more preferably less than about 10%, by weight based on the total weight of the hydrophilic polymer.

One preferred class of hydrophilic polymers as hydrophilicity-enhancing agents are (primary or secondary) amino- or carboxyl-containing polysaccharides, for example, such as, carboxymethylcellulose (having a carboxyl content of about 40% or less, which is estimated based on the composition of repeating units, —[$C_6H_{10-m}O_5(CH_2CO_2H)_m$]— in which m is 1 to 3), carboxyethylcellulose (having a carboxyl content of about 36% or less, which is estimated based on the composition of repeating units, —[$C_6H_{10-m}O_5(C_2H_4CO_2H)_m$]— in which m is 1 to 3) carboxypropylcellulose (having a carboxyl content of about 32% or less, which is estimated based on the composition of repeating units, —[$C_6H_{10-m}O_5(C_3H_6CO_2H)_m$]—, in which m is 1 to 3), hyaluronic acid (having a carboxyl content of about 11%, which is estimated based on the composition of repeating units, —($C_{13}H_{20}O_9NCO_2H$)—), chondroitin sulfate (having a carboxyl content of about 9.8%, which is estimated based on the composition of repeating units, —($C_{12}H_{18}O_{13}NSCO_2H$)—), or combinations thereof.

Another preferred class of hydrophilic polymers as hydrophilicity-enhancing agents include without limitation: poly(ethylene glycol) (PEG) with mono-amino (primary or secondary amino), carboxyl or thiol group (e.g., PEG-NH$_2$, PEG-SH, PEG-COOH); H$_2$N-PEG-NH$_2$; HOOC-PEG-COOH; HS-PEG-SH; H$_2$N-PEG-COOH; HOOC-PEG-SH; H$_2$N-PEG-SH; multi-arm PEG with one or more amino (primary or secondary), carboxyl or thiol groups; PEG dendrimers with one or more amino (primary or secondary), carboxyl or thiol groups; a diamino-(primary or secondary) or dicarboxyl-terminated homo- or co-polymer of a non-reactive hydrophilic vinylic monomer; a monoamino- (primary or secondary) or monocarboxyl-terminated homo- or co-polymer of a non-reactive hydrophilic vinylic monomer; a copolymer which is a polymerization product of a composition comprising (1) about 60% by weight or less, preferably from about 0.1% to about 30%, more preferably from about 0.5% to about 20%, even more preferably from about 1% to about 15%, by weight of one or more reactive vinylic monomers and (2) at least one non-reactive hydrophilic vinylic monomer; and combinations thereof.

In accordance with the invention, reactive vinylic monomers can be carboxyl-containing vinylic monomers, primary amino-containing vinylic monomers, or secondary amino-containing vinylic monomers.

Examples of preferred carboxyl-containing vinylic monomers include without limitation acrylic acid, methacrylic ethylacrylic acid, N-2-(meth)acrylamidoglycolic acid, and combinations thereof.

Examples of preferred primary and secondary amino-containing vinylic monomers include without limitation N-2-aminoethyl (meth)acrylamide, N-2-methylaminoethyl (meth)acrylamide, N-2-ethylaminoethyl (meth)acrylamide, N-3-aminopropyl (meth)acrylamide, N-3-methylaminopropyl (meth)acrylamide, 2-aminoethyl (meth)acrylate, 2-methylaminoethyl (meth)acrylate, 2-ethylaminoethyl (meth)acrylate, 3-aminopropyl (meth)acrylate, 3-methylaminopropyl (meth)acrylate, 3-ethylaminopropyl (meth)acrylate, 3-amino-2-hydroxypropyl (meth)acrylate, and combinations thereof.

In accordance with the invention, a non-reactive vinylic monomer is a vinylic monomer free of any carboxyl group, primary amino group, secondary amino group, epoxide group, isocyanate group, azlactone group, or aziridine group. Non-reactive vinylic monomers preferably are non-charged hydrophilic vinylic monomers which are free of carboxyl or amino group (any those described above can be used here), phosphorylcholine-containing vinylic monomers (any those described above can be used here), or combinations thereof.

More preferably, a hydrophilic polymer as a hydrophilicity-enhancing agent is:

a poly(ethylene glycol) having one sole functional group of —$NH_2$, —SH or —COOH;

a poly(ethylene glycol) having two terminal functional groups selected from the group consisting of —$NH_2$, —COOH, —SH, and combinations thereof;

a multi-arm poly(ethylene glycol) having one or more functional groups selected from the group consisting of —$NH_2$, —COOH, —SH, and combinations thereof;

a monoamino-, monocarboxyl-, diamino- or dicarboxyl-terminated homo- or copolymer of a non-reactive hydrophilic vinylic monomer;

a copolymer which is a polymerization product of a composition comprising (1) from about 0.1% to about 30%, preferably from about 0.5% to about 20%, more preferably from about 1% to about 15%, by weight of acrylic acid, methacrylic acid, ethylacrylic acid, 2-(meth)acrylamidoglycolic acid, N-2-aminoethyl (meth)acrylamide, N-2-methylaminoethyl (meth)acrylamide, N-2-ethylaminoethyl (meth)acrylamide, N-3-aminopropyl (meth)acrylamide, N-3-methylaminopropyl (meth)acrylamide, 2-aminoethyl (meth)acrylate, 2-methylaminoethyl (meth)acrylate, 2-ethylaminoethyl (meth)acrylate, 3-aminopropyl (meth)acrylate, 3-methylaminopropyl (meth)acrylate, 3-amino-2-hydroxypropyl (meth)acrylate, or a combination thereof, and (2) at least one non-reactive hydrophilic vinylic monomer selected from the group consisting of acryamide, N,N-dimethylacrylamide, N-vinylpyrrolidone, (meth)acryloyloxyethyl phosphorylcholine, N-vinyl-N-methyl acetamide, glycerol (meth)acrylate, hydroxyethyl (meth)acrylate, N-hydroxyethyl (meth)acrylamide, $C_1$-$C_4$-alkoxy polyethylene glycol (meth)acrylate having a weight average molecular weight of up to 400 Daltons, vinyl alcohol, and combination thereof, wherein the non-reactive hydrophilic vinylic monomer selected from the group consisting of selected from the group consisting of alkyl (meth)acrylamides (any one described above), N-2-dimethylaminoethyl (meth)acrylamide, dimethylaminoethyl (meth)acrylate, hydroxyl-containing acrylic monomers (any one described above), N-vinyl amide monomers (any one described above), methylene-containing pyrrolidone monomers (i.e., pyrrolidone derivatives each having a methylene group connected to the pyrrolidone ring at 3- or 5-position) (any one described above), acrylic monomers having a $C_1$-$C_4$ alkoxyethoxy group (any one described above), vinyl ether monomers (any one described above), allyl ether monomers (any one described above), a phosphorylcholine-containing vinylic monomer (any one described above) and combinations thereof (preferably selected from the group consisting of (meth)acryloyloxyethyl phosphorylcholine, (meth)acryloyloxypropyl phosphorylcholine, 4-((meth)acryloyloxy)butyl-2'-(trimethylammonio)ethylphosphate, 2-[(meth)acryloylamino]ethyl-2'-(trimethylammonio)ethylphosphate, 3-[(meth)acryloylamino]propyl-2'-(trimethylammonio)ethylphosphate, 4-[(meth)acryloylamino]butyl-2'-(trimethylammonio)ethylphosphate, (meth)acrylamide, dimethyl (meth)acrylamide, N-2-hydroxylethyl (meth)acrylamide, N,N-bis(hydroxyethyl) (meth)acrylamide, N-2,3-dihydroxypropyl (meth)acrylamide, N-tris(hydroxymethyl) methyl (meth)acrylamide, 2-hydroxyethyl (meth)acrylate, glycerol methacrylate (GMA), tetra(ethylene glycol) (meth)acrylate, poly(ethylene glycol)ethyl (meth)acrylamide having a number average molecular weight of up to 1500, poly(ethylene glycol) (meth)acrylate having a number average molecular weight of up to 1500, N-vinylpyrrolidone, N-vinyl-N-methyl acetamide, N-vinyl formamide, N-vinyl acetamide, 1-methyl-3-methylene-2-pyrrolidone, 1-methyl-5-methylene-2-pyrrolidone, 5-methyl-3-methylene-2-pyrrolidone, tetra(ethylene glycol) methyl ether (meth)acrylate, methoxypoly(ethylene glycol)ethyl (meth)acrylamide having a number average molecular weight of up to 1500, $C_1$-$C_4$-alkoxy polyethylene glycol (meth)acrylate having a weight average molecular weight of up to 1500, tetra(ethylene glycol) monovinyl ether, poly(ethylene glycol) monovinyl ether, tetra(ethylene glycol) methyl vinyl ether, poly(ethylene glycol) methyl vinyl ether, tetra(ethylene glycol) monoallyl ether, poly(ethylene glycol) monoallyl ether, tetra(ethylene glycol) methyl allyl ether, poly(ethylene glycol) methyl allyl ether, vinyl alcohol, allyl alcohol, and combinations thereof, more preferably selected from the group consisting of (meth)acryloyloxyethyl phosphorylcholine, (meth)acryloyloxypropyl phosphorylcholine, 4-((meth)acryloyloxy)butyl-2'-(trimethylammonio)ethylphosphate, 2-[(meth)acryloylamino]ethyl-2'-(trimethylammonio)ethylphosphate, 3-[(meth)acryloylamino]propyl-2'-(trimethylammonio)ethylphosphate, 4-[(meth)acryloylamino]butyl-2'-(trimethylammonio)ethylphosphate, (meth)acrylamide, dimethyl (meth)acrylamide, N-2-hydroxylethyl (meth)acrylamide, N,N-bis(hydroxyethyl) (meth)acrylamide, N-2,3-dihydroxypropyl (meth)acrylamide, N-tris(hydroxymethyl) methyl (meth)acrylamide, 2-hydroxyethyl (meth)acrylate, glycerol methacrylate (GMA), poly(ethylene glycol)ethyl (meth)acrylamide having a number average molecular weight of up to 1500, poly(ethylene glycol) (meth)acrylate having a number average molecular weight of up to 1500, N-vinylpyrrolidone, N-vinyl-N-methyl acetamide, methoxypoly(ethylene glycol)ethyl (meth)acrylamide having a number average molecular weight of up to 1500, methoxy polyethylene glycol (meth)acrylate having a weight average molecular weight of up to 1500, poly(ethylene glycol) monovinyl ether, poly(ethylene glycol) methyl vinyl ether, poly(ethylene glycol) monoallyl ether, poly(ethylene glycol) methyl allyl ether, vinyl alcohol, allyl alcohol, and combinations thereof, even more preferably selected from the group consisting of (meth)acryloyloxyethyl phosphorylcholine, (meth)acryloyloxypropyl phosphorylcholine, 2-[(meth)acryloylamino]ethyl-2'-(trimethylammonio)ethylphosphate, 3-[(meth)acryloylamino]propyl-2'-(trimethylammonio)ethylphosphate, (meth)acrylamide, dimethyl (meth)acrylamide, N-2-hydroxylethyl (meth)acrylamide, N,N-bis(hydroxyethyl) (meth)acrylamide, N-2,3-dihydroxypropyl (meth)acrylamide, N-tris(hydroxymethyl) methyl (meth)acrylamide, poly(ethylene glycol)ethyl (meth)acrylamide having a number average molecular weight of up to 1500, poly(ethylene glycol) (meth)acrylate having a number average molecular weight of up to 1500, N-vinylpyrrolidone, N-vinyl-N-methyl acetamide, methoxypoly(ethylene glycol)ethyl (meth)acrylamide having a number average molecular weight of up to 1500, methoxy polyethylene glycol (meth)acrylate having a weight average molecular weight of up to 1500, and combinations thereof.

PEGs with functional groups and multi-arm PEGs with functional groups can be obtained from various commercial suppliers, e.g., Creative PEGWorks, Polyscience, and Shearwater Polymers, etc.

Monoamino-, monocarboxyl-, diamino- or dicarboxyl-terminated homo- or copolymers of one or more non-reactive hydrophilic vinylic monomers or of a phosphorylcholine-containing vinylic monomer can be prepared according to procedures described in U.S. Pat. No. 6,218,508. For example, to prepare a diamino- or dicarboxyl-terminated homo- or co-polymer of a non-reactive hydrophilic vinylic monomer, the non-reactive vinylic monomer, a chain transfer agent with an amino or carboxyl group (e.g., 2-aminoethanethiol, 2-mercaptopropinic acid, thioglycolic acid, thiolactic acid, or other hydroxymercaptanes, aminomercaptans, or carboxyl-containing mercaptanes) and optionally other vinylic monomer are copolymerized (thermally or actinically) with a reactive vinylic monomer (having an amino or carboxyl group), in the presence of an free-radical initiator. Generally, the molar ratio of chain transfer agent to that of all of vinylic monomers other than the reactive vinylic monomer is from about 1:5 to about 1:100, whereas the molar ratio of chain transfer agent to the reactive vinylic monomer is 1:1. In such preparation, the chain transfer agent with amino or carboxyl group is used to control the molecular weight of the resultant hydrophilic polymer and forms a terminal end of the resultant hydrophilic polymer so as to provide the resultant hydrophilic polymer with one terminal amino or carboxyl group, while the reactive vinylic monomer provides the other terminal carboxyl or amino group to the resultant hydrophilic polymer. Similarly, to prepare a monoamino- or monocarboxyl-terminated homo- or co-polymer of a non-reactive hydrophilic vinylic monomer, the non-reactive vinylic monomer, a chain transfer agent with an amino or carboxyl group (e.g., 2-aminoethanethiol, 2-mercaptopropinic acid, thioglycolic acid, thiolactic acid, or other hydroxymercaptanes, aminomercaptans, or carboxyl-containing mercaptanes) and optionally other vinylic monomers are copolymerized (thermally or actinically) in the absence of any reactive vinylic monomer.

Copolymers comprising a non-reactive hydrophilic vinylic monomer and a reactive vinylic monomer (e.g., a carboxyl-containing vinylic monomer, a primary amino group-containing vinylic monomer or a secondary amino group-containing vinylic monomer) can be prepared according to any well-known radical polymerization methods or obtained from commercial suppliers. Copolymers containing methacryloyloxyethyl phosphorylcholine and carboxyl-containing vinylic monomer (or amino-containing vinylic monomer) can be obtained from NOF Corporation (e.g., LIPIDURE®-A and -AF) or prepared according to the procedures described in U.S. Pat. No. 9,127,099.

The weight average molecular weight $M_w$ of the hydrophilic polymer having at least one amino, carboxyl or thiol group (as a hydrophilicity-enhancing agent) is preferably from about 500 to about 5,000,000, more preferably from about 1,000 to about 2,000,000, even more preferably from about 5,000 to about 1,000,000 Daltons.

Water-soluble and thermally-crosslinkable hydrophilic polymeric materials can be prepared according to the processes disclosed in U.S. Pat. Appl. Pub. Nos. US 2016/0061995 A1 and US2013/0337160 A1 and in U.S. Pat. No. 8,529,057.

In a preferred embodiment, the aqueous reactive solution comprises from 0.01% to about 10% by weight (preferably from 0.05% to about 5% by weight, more preferably from 0.08% to about 1% by weight, even more preferably from 0.1% to about 0.4% by weight) of an azetidinium-containing polymer and from about 0.01% to about 10% by weight (preferably from 0.02% to about 5% by weight, more preferably from 0.05% to about 2% by weight, even more preferably from 0.08% to about 1.0% by weight) of a hydrophilicity-enhancing agent having at least one reactive function group (carboxyl, primary amino, secondary amino group), the concentration ratio of the azetidinium-containing polymer to the hydrophilicity-enhancing agent is from about 1000:1 to 1:1000 (preferably from about 500:1 to about 1:500, more preferably from about 250:1 to about 1:250, even more preferably from about 100:1 to about 1:100).

In a preferred embodiment, the water-soluble thermally-crosslinkable polymeric material comprises (i) from about 20% to about 95% by weight of first polymer chains derived from a polyamidoamine-epichlorohydrin or a poly(2-oxazoline-co-ethyleneimine)-epichlorohydrn, (ii) from about 5% to about 80% by weight of hydrophilic moieties or second polymer chains derived from at least one hydrophilicity-enhancing agent having at least one reactive functional group selected from the group consisting of amino group, carboxyl group, thiol group, and combination thereof (preferably carboxyl or thiol groups), wherein the hydrophilic moieties or second polymer chains are covalently attached to the first polymer chains through one or more covalent linkages each formed between one azetitdinium group of the polyamidoamine-epichlorohydrin or the poly(2-oxazoline-co-ethyleneimine)-epichlorohydrin and one amino, carboxyl or thiol group of the hydrophilicity-enhancing agent, and (iii) azetidinium groups which are parts of the first polymer chains or pendant or terminal groups covalently attached to the first polymer chains. The composition of a chemically-modified poly(2-oxazoline-co-ethyleneimine)-epichlorohydrin or a chemically-modified polyamidoamine-epichlorohydrin is determined by the composition (based on the total weight of the reactants) of a reactant mixture used for such a polymer according to the crosslinking reactions shown in Scheme I above. For example, if a reactant mixture comprises about 75% by weight of a polyamidoamine-epichlorohydrin and about 25% by weight of at least one hydrophilicity-enhancing agent based on the total weight of the reactants, then the resultant chemically-modified polyamidoamine-epichlorohydrin comprises about 75% by weight of first polymer chains derived from the polyamioamine-epichlorohydrin and about 25% by weight of hydrophilic moieties or second polymer chains derived from said at least one hydrophilicity-enhancing agent.

In accordance with the invention, the treated SiHy contact lens with a base coating thereon is heated in an aqueous solution which comprises a thermally-crosslinkable hydrophilic polymeric material having azetidinium groups and optionally (but preferably) amino groups, thiol groups, carboxyl groups or combinations thereof, at a temperature of from about 60° C. to about 140° C. for a time period to crosslink the thermally-crosslinkable hydrophilic polymeric material while covalently attaching the crosslinked thermally-crosslinkable hydrophilic polymeric material onto the anchor layer so as to form a water gradient SiHy contact lens.

Preferably, the step of heating is performed by autoclaving the treated SiHy contact lens with a base coating thereon immersed in the aqueous coating solution which is a packaging solution (i.e., a buffered aqueous solution with a pH of from 6.7 to 7.6) in a sealed lens package at a temperature of from about 115° C. to about 125° C. for approximately 20-90 minutes. It is believed that during autoclave those azetidinium groups which do not participate in crosslinking reaction may be hydrolyzed into 2,3-dihydroxypropyl (HO—CH—CH(OH)—CH$_2$—) groups and that the azetidinium-containing polymeric material present in the lens packaging solution, if applicable, can be converted to a non-reactive polymeric wetting agent capable of improving a lens's insert comfort. Consequently, the second aqueous coating solution is ophthalmically safe after autoclave.

Lens packages (or containers) are well known to a person skilled in the art for autoclaving and storing a contact lens. Any lens packages can be used in the invention.

Preferably, a lens package is a blister package which comprises a base and a cover, wherein the cover is detachably sealed to the base, wherein the base includes a cavity for receiving a sterile packaging solution and the contact lens.

Lenses are packaged in individual packages, sealed, and sterilized (e.g., by autoclave at about 120° C. or higher for at least 30 minutes under pressure) prior to dispensing to users. A person skilled in the art will understand well how to seal and sterilize lens packages.

In accordance with the invention, a packaging solution contains at least one buffering agent and one or more other ingredients known to a person skilled in the art. Examples of other ingredients include without limitation, tonicity agents, surfactants, antibacterial agents, preservatives, and lubricants (e.g., cellulose derivatives, polyvinyl alcohol, polyvinyl pyrrolidone).

The packaging solution contains a buffering agent in an amount sufficient to maintain a pH of the packaging solution in the desired range, for example, preferably in a physiologically acceptable range of about 6.5 to about 7.5. Any known, physiologically compatible buffering agents can be used. Suitable buffering agents as a constituent of the contact lens care composition according to the invention are known to the person skilled in the art. Examples are boric acid, borates, e.g. sodium borate, citric acid, citrates, e.g. potassium citrate, bicarbonates, e.g. sodium bicarbonate, TRIS (2-amino-2-hydroxymethyl-1,3-propanediol), Bis-Tris (Bis-(2-hydroxyethyl)-imino-tris-(hydroxymethyl)-methane), bis-aminopolyols, triethanolamine, ACES (N-(2-hydroxyethyl)-2-aminoethanesulfonic acid), BES (N,N-Bis(2-hydroxyethyl)-2-aminoethanesulfonic acid), HEPES (4-(2-hydroxyethyl)-1-piperazineethanesulfonic acid), MES (2-(N-morpholino)ethanesulfonic acid), MOPS (3—[N-morpholino]-propanesulfonic acid), PIPES (piperazine-N,N'-bis(2-ethanesulfonic acid), TES (N-[Tris(hydroxymethyl)methyl]-2-aminoethanesulfonic acid), salts thereof, phosphate buffers, e.g. Na$_2$HPO$_4$, NaH$_2$PO$_4$, and KH$_2$PO$_4$ or mixtures thereof. Preferably, the buffering agents are phosphate buffers, borate buffers, or combinations thereof. The amount of each buffer agent in a packaging solution is preferably from 0.001% to 2%, preferably from 0.01% to 1%; most preferably from about 0.05% to about 0.30% by weight.

The packaging solution has a tonicity of from about 200 to about 450 milliosmol (mOsm), preferably from about 250 to about 350 mOsm. The tonicity of a packaging solution can be adjusted by adding organic or inorganic substances which affect the tonicity. Suitable occularty acceptable tonicity agents include, but are not limited to sodium chloride, potassium chloride, glycerol, propylene glycol, polyols, mannitol, sorbitol, xylitol and mixtures thereof.

A packaging solution of the invention has a viscosity of from about 1 centipoise to about 5 centipoises, at 25° C.

In a preferred embodiment, the packaging solution comprises preferably from about 0.01% to about 2%, more preferably from about 0.05% to about 1.5%, even more preferably from about 0.1% to about 1%, most preferably from about 0.2% to about 0.5%, by weight of a water-soluble thermally-crosslinkable hydrophilic polymeric material having azetidinium groups.

In any one of the preferred embodiments described above of the various aspects of the invention, a contact lens produced according to a process of the invention has a friction rating of about 2 or lower (preferably about 1.5 or lower, more preferably about 1.0 or lower, even more preferably about 0.5 or lower) after 30 cycles of digital rubbing test.

Although various embodiments of the invention have been described using specific terms, devices, and methods, such description is for illustrative purposes only. The words used are words of description rather than of limitation. As would be obvious to one skilled in the art, many variations and modifications of the invention may be made by those skilled in the art without departing from the spirit and scope of the novel concepts of the disclosure. In addition, it should be understood that aspects of the various embodiments of the invention may be interchanged either in whole or in part or can be combined in any manner and/or used together.

The previous disclosure will enable one having ordinary skill in the art to practice the invention. Various modifications, variations, and combinations can be made to the various embodiment described herein. In order to better enable the reader to understand specific embodiments and the advantages thereof, reference to the following examples is suggested. It is intended that the specification and examples be considered as exemplary.

Example 1

Chemicals

The following abbreviations are used in the following examples: NVP represents N-vinylpyrrolidone; MMA represents methyl methacrylate; TEGDMA represent triethyleneglycol dimethacrylate; VAZO 64 represents 2,2'-dimethyl-2,2'azodipropiononitrile; Nobloc is 2-[3-(2H-Benzotriazol-2-yl)-4-hydroxyphenyl]ethyl methacrylate from Aldrich; UV28 represents 2-{2'-Hydroxy-3'-tert-butyl-5'-[3'-methacryloyloxypropoxy]phenyl}-5-chloro-2H-benzotriazole; RB247 is Reactive Blue 247; TAA represents tert-amyl alcohol; PrOH represents 1-propanol; IPA represents isopropanol; PAA represents polyacrylic acid; PMAA represents polymethacrylic acid; PAE represents polyamidoamine-epichlorohydrin (a.k.a., polyamine-epichlorohydrin); MPC represent 2-methacryloyloxyethyl phosphorylcholine; Poly(AAm-co-AA) represents poly(acrylamide-co-acrylic acid); PBS represents a phosphate-buffered saline which has a pH of 7.2±0.2 at 25° C. and contains about 0.044 wt % NaH$_2$PO$_4$.H$_2$O, about 0.388 wt. % Na$_2$HPO$_4$.2H$_2$O, and about 0.79 wt. % NaCl and; wt. % represents weight percent; D9 represents monobutyl-terminated monomethacryloxypropyl-terminated polydimethylsiloxane (Mw~984 g/mol from Shin-Etsu); "G4" macromer represents a di-methacryloyloxypropyl-terminated polysiloxane (Mn~13.5K g/mol, OH content~1.8 meq/g) of formula (A).

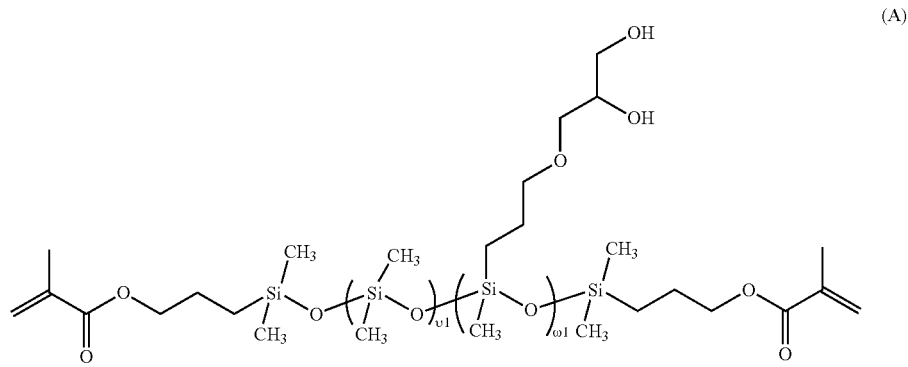

(A)

Oxygen Permeability Measurements

The apparent oxygen permeability ($Dk_{app}$), the apparent oxygen transmissibility (Dk/t), the intrinsic (or edge-corrected) oxygen permeability ($Dk_c$) of a lens and a lens material are determined according to procedures described in Example 1 of U.S. patent application publication No. 2012/0026457 A1 (herein incorporated by reference in its entirety).

Digital Rubbing Treatment

The lenses are digitally rubbed (wearing disposable powder-free latex gloves) with RENU® multi-purpose lens care solution (or another multi-purpose lens care solution) for 20 seconds and then rinsed with saline. The above procedure is repeated for i time (i.e., i cycles of digital rubbing) that imitates daily cleaning in a i-days lens care regime, e.g. 7 times (i.e., 7 cycles of digital rubbing) that imitates daily cleaning and disinfecting in a 7-days lens care regime), or 30 times (i.e., 30 cycles of digital rubbing) that imitates daily cleaning and disinfecting in a 30-days lens care regime.

Simulated Abrasion Cycling Treatment

To simulate a worst-case scenario for manual cycling, a simulated abrasion technique is used to ensure consistent pressure and shearing conditions. To do this, a customized lens holder is made to grip the lens while shearing the lens. As shown in FIG. 1, the lens (part 1) is placed on a rubber insert (part 2) with a 7.7 mm diameter central shaft (part 3) fitted axially. The top clip (part 4) is clipped onto the bottom clip (part 5), which holds the lens tightly against the silicone gasket. The central shaft is then extended so the lens is sticking above the outer body surface, exposing the lens circular area around the center of the lens. Optionally, a piece of cloth (i.e. Twillx 1622, Berkshire) can be placed between the central shaft and contact lens to enhance abrasion visualization.

The entire lens holder is placed on the attachment end of the Taber linear abrader system (Taber Industries, model 5750, http://www.taberindustries.com/linear-abraser). With no added weights are attached, the entire weight of the bearing arm and lens holder (230 g normal force) is applied to the 47 mm² contact lens area, allowing 49 kPa to be applied to the counter surface. For the counter surface, a sheet of silicone rubber (10 A, ¼ thick) is placed underneath the bearing arm, and a reservoir channel is clipped to the silicone rubber. The reservoir is then filled with PBS at room temperature.

During the experiment, the lens holder is slowly dropped to the counter surface, and the lens is abraded 20 times (3" per stroke, 6" total travel per cycle) at a frequency of 75 cycles per minute. The lens surface can be analyzed using the water break up time methodology, lubricity evaluation, and/or Sudan Black staining test.

While this technique applies a shear force well beyond what a typical contact lens would experience, this controlled shearing technique (i.e., simulated abrasion cycling treatment) is found to be a reasonable equivalent of 30 cycles of digital rubbing treatment and provides assurance that these contact lenses will be able to handle even the harshest mechanical cycling.

Lubricity Evaluation.

The lubricity of a contact lens is evaluated by using a finger-felt lubricity test which characterizes qualitatively the slipperiness of a lens surface on a friction rating scale of from 0 to 4. The higher the friction rating is, the lower the slipperiness (or lubricity).

Commercial lenses: DAILIES® TOTAL1®; ACUVUE® OASYS™; ACUVUE® ADVANCE PLUSM; DAILIES® Aqua Comfort Plus®; and AIR OPTIX®, are assigned a friction rating (designated "FR" hereinafter) of 0, 1, 2, 3, and 4 respectively. They are used as standard lenses for determining the friction rating of a lens under test.

The samples are placed in PBS (phosphate buffer saline having the following composition: 0.044 w/w % $NaH_2PO_4 \cdot H_2O$, ca. 0.388 w/w/% $Na_2HPO_4 \cdot 2H_2O$, and ca. 0.79 w/w % NaCl) for at least two rinses of 30 minutes each and then transferred to fresh PBS before the evaluation.

Before the evaluation, hands are rinsed with a soap solution, extensively rinsed with DI water and then dried with KimWipe® towels. The samples are handled between the fingers and a numerical number is assigned for each sample relative to the above standard lenses described above. For example, if lenses are determined to be only slightly better than AIR OPTIX® lenses, then they are assigned a number 3. The value of a friction rating is one obtained by averaging the results of at least two friction ratings of a contact lens by two or more persons and/or by averaging the friction ratings of two or more contact lenses (from the identical batch of lens production) by one person.

The finger lubricities (i.e., friction ratings) of a contact lens can be determined either directly out-of-pack (OOP) but after 230 min soaking in PBS) or after i cycles (e.g., 7, 14, 21, or 30 cycles) of digital rubbing treatment, or after simulated abrasion cycling treatment according to the procedures described above.

Water Break-Up Time (WBUT) Tests

The surface hydrophilicity of lenses (after autoclave) is assessed by determining the time required for the water film to start breaking on the lens surface. Lenses exhibiting WBUT≥10 seconds are considered to have a hydrophilic surface and are expected to exhibit adequate wettability (ability to support the tear film) on-eye.

Lenses are prepared for water breakup measurement by removing the lens from its blister with soft plastic tweezers (e.g., those from Menicon) and placing the lens in a test tube containing phosphate buffered saline. The test tube contains 10 mL phosphate buffered saline per lens, 1 lens per test tube. Lenses are soaked overnight (at least 16 hours) before testing.

WBUT is measured at room temperature as follows: the lens is removed from the test tube and placed on a pedestal submerged in PBS. The pedestal is then raised out of the PBS solution (t=0), and a video camera monitors the fluid flowing off the lens surface. When the lens surface fluid breaks, this WBUT time is recorded. Optionally, a stop watch can be used to measure the time between when the pedestal is raised out of the PBS and when the lens surface fluid breaks. The pedestal is withdrawn, pulling the lens beneath the surface of the PBS. At least 3 spots per lenses are measured, and at least 3 lenses are measured to obtain an average WBUT measurement for each lens group.

Equilibrium Water Content

The equilibrium water content (EWC) of contact lenses is determined as follows.

Amount of water (expressed as percent by weight) present in a hydrated hydrogel contact lens, which is fully equilibrated in saline solution, is determined at room temperature.

Quickly stack the lenses, and transfer the lens stack to the aluminum pan on the analytical balance after blotting lens in a cloth. The number of lenses for each sample pan is typically five (5). Record the pan plus hydrated weight of the lenses. Cover the pan with aluminum foil. Place pans in a laboratory oven at 100±2° C. to dry for 16-18 hours. Remove pan plus lenses from the oven and cool in a desiccator for at least 30 minutes. Remove a single pan from the desiccator, and discard the aluminum foil. Weigh the pan plus dried lens sample on an analytical balance. Repeat for all pans. The wet and dry weight of the lens samples can be calculated by subtracting the weight of the empty weigh pan.

Elastic Modulus

The elastic modulus of a contact lens is determined using a MTS insight instrument. The contact lens is first cut into a 3.12 mm wide strip using Precision Concept two stage cutter. Five thickness values are measured within 6.5 mm gauge length. The strip is mounted on the instrument grips and submerged in PBS with the temperature controlled at 21±2° C. Typically 5N Load cell is used for the test. Constant force and speed is applied to the sample until the sample breaks. Force and displacement data are collected by the TestWorks software. The elastic modulus value is calculated by the TestWorks software which is the slope or tangent of the stress vs. strain curve near zero elongation, in the elastic deformation region.

Determinations of Polyquaternium-1 Uptake (PU).

Polyquaternium-1 uptake by a contact lens is determined according to a DNA intercalation procedure based on a PicoGreen dsDNA assay kit (i.e. Quanti-iT PicoGreen dsDNA kit, ThermoFisher). Polyquaternium-1 uptake by a contact lens is determined as follows:

A basis solution is prepared by dissolving the following components in purified water 5 ppm myristamidopropyldimethylamine; 1000 ppm sodium decanoyl ethylenediamine triacetate; 83 ppm sodium citrate dehydrate; 1000 ppm NaCl; 1000 ppm Tetronic 1304; 1150 ppm sodium borate decahydrate; and 10000 ppm propylene glycol and then by adjusting pH to about 7.8.

The Polyquaternium-1 (PQ) testing solution is prepared by dissolving a desired amount in the basis solution prepared above to have 5 ppm PQ and then by adjusting pH to about 7.8 if necessary. A series of PQ standard solutions each having a concentration within a range are prepared to establish a calibration curve between 0 and 6 ppm (or higher) of PQ.

Contact lenses are removed from their individual lens packages and shaken in 25 ml PBS per lens for 30 minutes. The PBS-soaked lenses are blotted with a paper towel (preferably with W4 polypropylene towels from Kimberly Clark) with a fixed weight (i.e. 0.6 kg) before being incubated overnight.

A 24-well plate will be used in the overnight incubation experiment. The wells are divided into the following categories: negative-control wells each containing 0.5 mL of the basis solution and two blotted contact lenses fully immersed therein; positive-control wells each containing 0.5 mL of the polyquarternium-1 testing solution; samples wells each containing 0.5 mL of the polyquarternium-1 testing solution and two blotted contact lenses fully immersed therein; standard wells each containing 0.5 mL of one of one of the standard solutions. The 24-well plate then is shaken for 20 minutes on an orbital shaker and then sits on a bench top overnight (for 16-20 hours) at room temperature.

A 25 µL aliquot from each of the wells of the overnight incubated 24-well plate is added to a 96-well plate (e.g. DNA LoBind, Eppendorf) cell well containing 450 µL of a Lambda DNA solution (1 µg/mL Lambda DNA; 10 mM Tris-HCl; 1 mM EDTA; pH 7.5). The solution is mixed and incubated on an orbital shaker at 700-800 rpm for 60 minutes.

A 100 µL aliquot from each of the DNA-incubated cell wells are transferred to a 96-well plate (e.g., black opaque, med bind, Grenier). Then 100 µL of the PicoGreen solution (ThermoFisher, diluted with Tris-EDTA buffer [10 mM Tris-HCl, 1 mM EDTA, pH 7.5] per kit instructions) are added to each of those wells and mixed. The cell wells are then incubated on an orbital shaker for 5 minutes at 250 rpm. Each plate is read with a fluorescence plate reader (e.g., Victor X5 Plate Reader, Perkin Elmer) using standard fluorescence excitation and emission wavelengths for the PicoGreen. Each sample is compared against the linear fit of the standard curve to obtain final PQ concentration in each solution. The amount of PQ uptake per lens is obtained by multiplying the incubation volume and dividing by the number of lenses incubated. The PQ uptake by the lens is calculated to be the difference in [polyquarternium-1] between the DNA-incubated positive-control and sample solutions, times the incubation volume (0.5 mL) and divide by 2.

Coating Intactness Tests

The intactness of a coating on the surface of a contact lens can be tested according to Sudan Black stain test as follow. Contact lenses with a coating (an LbL coating, a plasma coating, a hydrogel coating, or any other coatings) are dipped into a Sudan Black dye solution (Sudan Black in the mixture ~80% mineral oil and ~20% vitamin E oil). Sudan Black dye is hydrophobic and has a great tendency to be adsorbed by a hydrophobic material or onto a hydrophobic lens surface or hydrophobic spots on a partially coated surface of a hydrophobic lens (e.g., silicone hydrogel contact lens). If the coating on a hydrophobic lens is intact, no staining spots should be observed on or in the lens. All of the lenses under test are fully hydrated. Visible fine lines on lens surface may indicate the presence of cracking of the crosslinked coatings.

Example 2

Preparation of Polymerizable Compositions

Lens formulations (polymerizable compositions), I to IV, are prepared to have compositions (in unit parts) as shown in Table 1.

TABLE 1

|  | Formulation I | Formulation II | Formulation III | Formulation IV |
|---|---|---|---|---|
| D9 | 33 | 33 | 33 | 33 |
| G4 | 10 | 10 | 10 | 10 |
| NVP | 46 | 46 | 46 | 46 |
| MMA | 10 | 10 | 10 | 10 |
| TEGDMA | 0.2 | 0.2 | 0.2 | 0.65 |
| Norbloc | 1.5 | 1.5 | 1.8 | 1.5 |
| UV28 | 0.26 | 0.26 | 0 | 0.4 |
| VAZO 64 | 0.5 | 0.5 | 0.5 | 0.5 |
| RB247 | 0.01 | 0.01 | 0.01 | 0.01 |
| TAA | 10 | 10 | 10 | 10 |
| Curing Profile | 55/80/100° C. 30 min/ 2 hr/ 30 min | 55/80/100° C. 40 min/ 40 min/ 40 min | 55/80/100° C. 30 min/ 30 min/ 120 min/ 30 min | 55/80/100° C. 30 min/ 120 min/ 30 min |

The formulations are prepared by adding listed components in their targeted amounts into a clean bottle, with a stir bar to mix at 600 rpm for 30 minutes at room temperature. After all the solid is dissolved, a filtration of the formulation is carried out by using 2.7 μm glass-microfiber-filter.

Cast-Molded Silicone Hydrogel Contact Lenses

A lens formulation is purged with nitrogen at room temperature for 30 to 35 minutes. The $N_2$-purged lens formulation is introduced into polypropylene molds and thermally cured in an oven under the following curing conditions: ramping from room temperature to a first temperature and then holding at the first temperature for a first curing time period; ramping from the first temperature to a second temperature and holding at the second temperature for a second curing time period; optionally ramping from the second temperature to a third temperature and holding at the third temperature for a third curing time period; and optionally ramping from the third temperature to a fourth temperature and holding at the fourth temperature for a fourth curing time period.

Lens molds are opened by using a demolding machine with a push pin. Lenses are pushed onto base curve molds with a push pin and then molds are separated into base curve mold halves and front curve mold halves. The base curve mold halves with a lens thereon are placed in an ultrasonic device (e.g., Dukane's single horn ultrasonic device). With a certain energy force, a dry state lens is released from mold.

In the subsequent examples, SiHy contact lenses prepared from formulation IV are used unless otherwise specified.

Example 3

Solution PMAA-1

Solution PMAA-1 is a solution of polymethacrylic acid (PMAA), which is prepared by adding adequate amount of PMAA (Mn~400-600 kDa, from ProChem.) in PrOH/water (50 wt % water) mixture to have a concentration of about 0.04 wt. %. After PMAA is fully dissolved, the pH is adjusted by adding formic acid to the PMAA solution to about 2. The prepared PMAA solution is filtered to remove any particulate or foreign matter.

Phosphate Buffered saline solution (PBS-1) for IPC saline preparation PBS-1 is prepared by dissolving $NaH_2PO_4.H_2O$, $Na_2HPO_4.2H_2O$ and in a given volume of purified water (distilled or deionized) to have the following composition: ca. 0.174 w/w % $NaH_2PO_4.H_2O$, ca. 0.711 w/w % $Na_2HPO_4.2H_2O$, and ca. 1.920 w/w % NaCl.

IPC Saline (IPC-1)

A copolymer, poly(2-methacryloyloxyethyl phosphorylcholine-co-2-aminoethylmethacrylate)(96/4 w/w) (i.e., poly(MPC-co-AEM), is prepared by thermal polymerizing a polymerizable composition comprising: about 96 wt % MPC; about 4 wt % AEM; about 0.02 wt % Vazo 56 [2,2'-Azobis(2-methylpropionamidine) dihydrochloride]; about 0.1 wt % chain transfer agent (HS—CH2CH2OH) in water at about 60° C. for about 2 hours and then at 20° C. for about 2 hours. The obtained poly(MPC-co-AEM) (an aqueous solution with solid content ~10%) is determined to have an amine functionality of ~0.22 meq/g, and a Mn of ~160 kDa and is concentrated by ultrafiltration.

Mix about 75 wt % of the poly(MPC-co-AEM) solution prepared above, about 4.6 wt % PAE solution (purchased from Ashland as an aqueous solution and used as received), and about 20 wt % of a phosphate salt solutions (about 0.22 wt % $NaH_2PO_4.H_2O$, 0.9 wt % $Na_2HPO_4.2H_2O$), Adjust pH to ~7.3 by 1N NaOH. React the mixture in a water bath at 60° C. for 4 hours to form water-soluble thermally-crosslinkable polymeric material (i.e., "in-package crosslinking agent) or "IPC agent"). Remove the mixture from water bath and cool down in a room temperature water bath. Dilute the mixture about 10 folds using PBS-1 and water and adjust pH to about 7.3 as needed. The final IPC saline may also contain low concentration of peroxide (e.g. 5 ppm) and sodium citrate dihydrate (e.g. 0.07%). Filter the mixture by 0.22 μm PES sterile filter unit.

Phosphate Buffered Solution (PB, ~15 mM, pH~7.8)

PB is prepared by dissolving NaH2PO4.H2O and Na2HPO4.2H2O, in a given volume of purified water (distilled or deionized) to have the following composition: ca. 0.028 wt/vol % $NaH_2PO_4.H_2O$ and ca. 0.231 wt/vol % $Na_2HPO_4.2H_2O$ with final solution pH ca. 7.8

Preparation of Water Gradient SiHy Contact Lenses (Lenses 3-1) (Control)

Water Gradient SiHy Contact lenses (Lenses 3-1) are prepared according to a method comprising one sole dip-coating step for forming the base coating as follows.

After de-molding, cast-molded SiHy contact lenses (prepared in Example 2) are extracted with PrOH for 180 minutes for lens extraction, dip-coated in the PMAA-1 prepared above for about 50 min or one hour, rinsed in PrOH/water (55/45) for about 25 min, rinsed with PB for about 50-60 minutes, and then are packaged/sealed in polypropylene lens packaging shells (blisters) with 0.65 mL of the IPC-1 saline (half of the IPC-1 saline is added prior to inserting the lens). The sealed lens packages are autoclaved for about 45 minutes at about 121° C., forming SiHy contact lenses with a cross-linked hydrophilic coating (i.e., a hydrogel coating) thereon.

Preparation of Water Gradient SiHy Contact Lenses (Lenses 3-2)

Water Gradient SiHy Contact lenses (Lenses 3-2) are prepared according to a method comprising at least two dip-coating steps and one buffered saline rinsing step between each pair of dip-coating steps for forming the base coating as follows.

After de-molding, cast-molded SiHy contact lenses (prepared in Example 2) are extracted with PrOH for 180 minutes for lens extraction, dip-coated in the PMAA-1 prepared above for about 25 minutes, rinsed in PB for about 10 min, rinsed in deionized (DI) H$_2$O for 10 minutes, then again dip-coated in PMAA-1 for 25 minutes and rinsed in PB twice for 25 minutes each. Then are packaged/sealed in polypropylene lens packaging shells (blisters) with 0.65 mL of the IPC-1 saline (half of the IPC-1 saline is added prior to inserting the lens). The sealed lens packages are autoclaved for about 45 minutes at about 121° C., forming SiHy contact lenses with a cross-linked hydrophilic coating (i.e., a hydrogel coating) thereon.

Characterization of Resultant Water Gradient SiHy Contact Lenses

Resultant water gradient SiHy contact lenses are tested for the following properties: lubricity by friction rating; PU; coating intactness by Sudan Black (SB) Staining test; and WBUT, according to the procedures described in Example 1. The lenses are tested directly out of package (DOOP), or after being subjected to 30 cycles of digital rubbing treatment (30 DRT), or after being subjected to Simulated Abrasion Cycling Treatment (SACT), according to the procedures described in Example 1. The results are reported in Table 2.

TABLE 2

| Lenses | Optical power (diopter) | Friction rating | PU µg/lens | SB Staining DOOP | SB Staining 30 DRT | WBUT (s) SACT |
|---|---|---|---|---|---|---|
| 3-1 | −3.00 | 0 | 0.20 ± 0.02 | no | light | 11 ± 4.2 |
| 3-1 | −12.00 | 0 | 0.14 ± 0.02 | no | light | 5 ± 2.3 |
| 3-2 | −3.00 | 0 | 0.34 ± 0.03 | no | no | 20 ± 2.4 |
| 3-2 | −2.00 | 0 | 0.25 ± 0.05 | no | no | 16 ± 4.4 |

The results in Table 2 indicate that both methods can produce water gradient SiHy contact lenses with good lubricity (a friction rating of about 0). But, a method of the invention can be used to produce water gradient contact lenses (lenses 3-2) with more durable hydrogel coating thereon, as shown by passing Sudan black staining test (no SB staining) after 30 cycles of digital rubbing treatment and by having a longer WBUT after Simulated Abrasion Cycling Treatment, compared to lenses produced by a control method.

Example 4

SBC Solution: 0.1% Sodium Bicarbonate Rinse Solution

SBC rinse solution is prepared by dissolving sodium bicarbonate in a given volume of purified water (distilled or deionized) to have the following composition: ca. 0.1 w/w % NaHCO$_3$.

Preparation of Water Gradient SiHy Contact Lenses (Lenses 4-1) (Control)

Water Gradient SiHy Contact lenses (Lenses 4-1) are prepared according to a method comprising one sole dip-coating step for forming the base coating as follows.

After de-molding, cast-molded SiHy contact lenses (prepared in Example 2) are extracted with PrOH for 180 minutes for lens extraction, dip-coated in the PMAA-1 prepared above for about 50 min or one hour, rinsed in SBC for about 50-60 minutes, and then are packaged/sealed in polypropylene lens packaging shells (blisters) with 0.65 mL of the IPC-25 saline (half of the IPC-25 saline is added prior to inserting the lens). The sealed lens packages are autoclaved for about 45 minutes at about 121° C., forming SiHy contact lenses with a cross-linked hydrophilic coating (i.e., a hydrogel coating) thereon.

Preparation of Water Gradient SiHy Contact Lenses (Lenses 4-2)

Water Gradient SiHy Contact lenses (Lenses 4-2) are prepared according to a method comprising at least two dip-coating steps and one saline rinsing step between each pair of dip-coating steps for forming the base coating as follows.

After de-molding, cast-molded SiHy contact lenses (prepared in Example 2) are extracted with n-propanol (PrOH) for 180 minutes for lens extraction, dip-coated in the PMAA-1 prepared in Example 3 for about 25 minutes, rinsed in SBC for about 10 min, rinsed in DI H2O for 10 minutes, then again dip-coated in PMAA-1 for 25 minutes and rinsed in SBC twice for 25 minutes each. Then are packaged/sealed in polypropylene lens packaging shells (blisters) with 0.65 mL of the IPC-1 saline (half of the IPC-1 saline is added prior to inserting the lens). The sealed lens packages are autoclaved for about 45 minutes at about 121° C., forming SiHy contact lenses with a cross-linked hydrophilic coating (i.e., a hydrogel coating) thereon.

Characterization of Resultant Water Gradient SiHy Contact Lenses

Resultant water gradient SiHy contact lenses are tested for the following properties: lubricity by friction rating; PU; coating intactness by Sudan Black (SB) Staining test; and WBUT, according to the procedures described in Example 1. The lenses are tested directly out of package (DOOP), or after being subjected to 30 cycles of digital rubbing treatment (30 DRT), according to the procedures described in Example 1. The results are reported in Table 3.

TABLE 3

| Lenses | Optical power (diopter) | Friction rating | PU µg/lens | SB Staining DOOP | SB Staining 30 DRT |
|---|---|---|---|---|---|
| 4-1 | −3.00 | 0 | 0.25 ± 0.01 | no | light |
| 4-1 | −12.00 | 0 | 0.16 ± 0.03 | no | heavy |
| 4-2 | −3.00 | 0 | 0.22 ± 0.02 | no | no |
| 4-2 | −12.00 | 0 | 0.20 ± 0.02 | no | no |

The results in Table 3 indicate that both methods can produce water gradient SiHy contact lenses with good lubricity (a friction rating of about 0). But, a method of the invention can be used to produce water gradient contact lenses (lenses 4-2) with more durable hydrogel coating thereon, as shown by passing Sudan black staining test (no SB staining) after 30 cycles of digital rubbing treatment, compared to lenses produced by a control method.

Example 5

PMAA Solution (PMAA-2):

A solution of polymethacrylic acid (PMAA) is prepared by adding adequate amount of PMAA (Mn~400-600 kDa, from ProChem.) in PrOH/water (50 wt % water) mixture to have a concentration of about 0.04 wt. %. After PMAA is fully dissolved, the pH is adjusted by adding sulfuric acid to the PMAA solution to about 2. The prepared PMAA solution is filtered to remove any particulate or foreign matter.

SBC Solution: 0.1% Sodium Bicarbonate Rinse Solution

SBC rinse solution is prepared by dissolving sodium bicarbonate in a given volume of purified water (distilled or deionized) to have the following composition: ca. 0.1 w/w % NaHCO$_3$.

Preparation of Water Gradient SiHy Contact Lenses (Lenses 5-1) (Control)

Water Gradient SiHy Contact lenses (Lenses 5-1) are prepared according to a method comprising one sole dip-coating step for forming the base coating as follows.

After de-molding, cast-molded SiHy contact lenses (prepared in Example 2) are extracted with PrOH for 180 minutes for lens extraction, dip-coated in the PMAA-2 prepared above for about 50 min or one hour, rinsed in SBC for about 50-60 minutes, and then are packaged/sealed in polypropylene lens packaging shells (blisters) with 0.65 mL of the IPC-1 saline (half of the IPC-1 saline is added prior to inserting the lens). The sealed lens packages are autoclaved for about 45 minutes at about 121° C., forming SiHy contact lenses with a cross-linked hydrophilic coating (i.e., a hydrogel coating) thereon.

Preparation of Water Gradient SiHy Contact Lenses (Lenses 5-2)

Water Gradient SiHy Contact lenses (Lenses 5-2) are prepared according to a method comprising at least two dip-coating steps and one saline rinsing step between each pair of dip-coating steps for forming the base coating as follows.

After de-molding, cast-molded SiHy contact lenses (prepared in Example 2) are extracted with PrOH for 180 minutes for lens extraction, dip-coated in the PMAA-2 prepared above for about 25 minutes, rinsed in SBC for about 10 min, rinsed in DI H2O for 10 minutes, then again dip-coated in PMAA-2 for 25 minutes and rinsed in SBC twice for 25 minutes each. Then are packaged/sealed in polypropylene lens packaging shells (blisters) with 0.65 mL of the IPC-1 saline (half of the IPC-1 saline is added prior to inserting the lens). The sealed lens packages are autoclaved for about 45 minutes at about 121° C., forming SiHy contact lenses with a cross-linked hydrophilic coating (i.e., a hydrogel coating) thereon.

Characterization of Resultant Water Gradient SiHy Contact Lenses

Resultant water gradient SiHy contact lenses are tested for the following properties: lubricity by friction rating; PU; coating intactness by Sudan Black (SB) Staining test; and WBUT, according to the procedures described in Example 1. The lenses are tested directly out of package (DOOP), or after being subjected to 30 cycles of digital rubbing treatment (30 DRT), or after being subjected to Simulated Abrasion Cycling Treatment (SACT), according to the procedures described in Example 1. The results are reported in Table 4.

TABLE 4

| Lenses | Optical power (diopter) | Friction rating | PU μg/lens | SB Staining DOOP | SB Staining 30 DRT | WBUT (s) SACT |
|---|---|---|---|---|---|---|
| 5-1 | −3.00 | 0 | 0.24 ± 0.07 | no | light | 15 ± 2.9 |
| 5-1 | −12.00 | 0 | 0.16 ± 0.02 | no | light | 7 ± 1.9 |
| 5-2 | −3.00 | 0 | 0.14 ± 0.05 | no | no | 17 ± 5.4 |
| 5-2 | −2.00 | 0 | 0.13 ± 0.04 | no | no | 11 ± 5.7 |

The results in Table 4 indicate that both methods can produce water gradient SiHy contact lenses with good lubricity (a friction rating of about 0). But, a method of the invention can be used to produce water gradient contact lenses (lenses 5-2) with more durable hydrogel coating thereon, as shown by passing Sudan black staining test (no SB staining) after 30 cycles of digital rubbing treatment and by having a longer WBUT after Simulated Abrasion Cycling Treatment, compared to lenses produced by a control method.

Example 6

PMAA Solution (PMAA-2):

A solution of polymethacrylic acid (PMAA) is prepared by adding adequate amount of PMAA (Mn~400-600 kDa, from ProChem.) in PrOH/water (50 wt % water) mixture to have a concentration of about 0.04 wt. %. After PMAA is fully dissolved, the pH is adjusted by adding sulfuric acid to the PMAA solution to about 2. The prepared PMAA solution is filtered to remove any particulate or foreign matter.

SBC Solution: 0.1% Sodium Bicarbonate Rinse Solution

SBC rinse solution is prepared by dissolving sodium bicarbonate in a given volume of purified water (distilled or deionized) to have the following composition: ca. 0.1 w/w % NaHCO$_3$.

Preparation of Water Gradient SiHy Contact Lenses (Lenses 6-1)

Water Gradient SiHy Contact lenses (Lenses 6-1) are prepared according to a method comprising at least two dip-coating steps and one saline rinsing step between each pair of dip-coating steps for forming the base coating as follows.

After de-molding, cast-molded SiHy contact lenses (prepared in Example 2) are extracted with PrOH for 180 minutes for lens extraction, dip-coated in the PMAA-2 prepared above for about 25 minutes, rinsed in SBC for about 10 min, rinsed in DI H2O for 10 minutes, then again dip-coated in PMAA-2 for 25 minutes and rinsed in SBC twice for 25 minutes each. Then are packaged/sealed in polypropylene lens packaging shells (blisters) with 0.65 mL of the IPC-1 saline (half of the IPC-1 saline is added prior to inserting the lens). The sealed lens packages are autoclaved for about 45 minutes at about 121° C., forming SiHy contact lenses with a cross-linked hydrophilic coating (i.e., a hydrogel coating) thereon. The coating uniformity or intactness is tested by Sudan black dye testing and the coating passed Sudan black dye testing.

Water Gradient SiHy Contact Lenses (Lenses 6-2)

Water Gradient SiHy Contact lenses (Lenses 6-2) are prepared according to a method comprising at least two dip-coating steps and one saline rinsing step between each pair of dip-coating steps for forming the base coating as follows.

After de-molding, cast-molded SiHy contact lenses (prepared in Example 2) are extracted with PrOH for 180 minutes for lens extraction, dip-coated in the PMAA-2 prepared above for about 25 minutes, rinsed in SBC for about 20 min, rinsed in DI H2O for 10 minutes, then again dip-coated in PMAA-2 for 25 minutes and rinsed in SBC twice for 25 minutes each. Then are packaged/sealed in polypropylene lens packaging shells (blisters) with 0.65 mL of the IPC-1 saline (half of the IPC-1 saline is added prior to inserting the lens). The sealed lens packages are autoclaved for about 45 minutes at about 121° C., forming SiHy contact lenses with a cross-linked hydrophilic coating (i.e., a hydrogel coating) thereon. The coating uniformity or intactness is tested by Sudan black dye testing and the coating passed Sudan black dye testing.

Characterization of Resultant Water Gradient SiHy Contact Lenses

Resultant water gradient SiHy contact lenses are tested for the following properties: lubricity by friction rating; PU; coating intactness by Sudan Black (SB) Staining test; and WBUT, according to the procedures described in Example 1. The lenses are tested directly out of package (DOOP), or after being subjected to 30 cycles of digital rubbing treatment (30 DRT), or after being subjected to Simulated Abrasion Cycling Treatment (SACT), according to the procedures described in Example 1. The results are reported in Table 5.

TABLE 5

| Lenses | Optical power (diopter) | Friction rating | PU pg/lens | SB Staining DOOP | SB Staining 30 DRT | WBUT (s) SACT |
|---|---|---|---|---|---|---|
| 6-1 | −3.00 | 0 | 0.21 ± 0.03 | no | no | 11 ± 4.2 |
| 6-1 | −12.00 | 0 | 0.18 ± 0.03 | no | no | 5 ± 2.3 |
| 6-2 | −3.00 | 0 | 0.23 ± 0.05 | no | no | 19 ± 5.2 |
| 6-2 | −2.00 | 0 | 0.21 ± 0.05 | no | no | 17 ± 5.5 |

The results in Table 5 indicate that the duration of saline-rinsing step can affect to some extent the durability as shown by having a longer WBUT after Simulated Abrasion Cycling Test for lenses 6-2 which are produce according to a method comprising a longer saline rinsing step between two dip-coating steps.

All the publications, patents, and patent application publications, which have been cited herein above in this application, are hereby incorporated by reference in their entireties.

What is claimed is:

1. A method for producing coated SiHy contact lenses each having a hydrogel coating thereon, comprising the steps of:
   (1) obtaining a preformed SiHy contact lens comprising a silicone hydrogel material as lens bulk material;
   (2) forming a base coating on the preformed SiHy contact lens according to a solution-coating procedure to form a treated SiHy contact lens having the base coating thereon, wherein the solution-coating procedure comprises the sub-steps of
      (a) contacting the preformed SiHy contact lens with a first coating solution for a first coating period of time, wherein the first coating solution has a first pH and comprises from about 0.001% to about 5.0% by weight of a first polyanionic polymer,
      (b) rinsing the preformed SiHy contact lens obtained in sub-step (a) with a first buffered saline having a second pH for a first rinsing period of time,
      (c) optionally rinsing the preformed SiHy contact lens obtained in sub-step (b) with water, one or more organic solvent miscible with water, or a mixture thereof for a second rinsing period of time,
      (d) contacting the preformed SiHy contact lens obtained in sub-step (b) or (c) with a second coating solution for a second coating period of time, wherein the second coating solution has a third pH and comprises from about 0.001% to about 5.0% by weight of a second polyanionic polymer,
      (e) rinsing the preformed SiHy contact lens obtained in sub-step (d) with a second buffered saline having a fourth pH for a third rinsing period of time, and
      (f) optionally rinsing the preformed SiHy contact lens obtained in sub-step (e) with water, one or more organic solvent miscible with water, or a mixture thereof for a fourth rinsing period of time,
   wherein the first and second polyanionic polymer independent of each other are a homo- or copolymer of acrylic acid or $C_1$-$C_3$ alkylacrylic acid, wherein the first pH and the third pH independent of each other are from 0 to about 4.5, wherein the second pH and the fourth pH independent of each other are from about 6.5 to about 10; and
   (3) heating the treated SiHy contact lens having the base coating thereon in an aqueous solution having a pH of from about 6.5 to about 9.5 and including a water-soluble, thermally-crosslinkable hydrophilic polymeric material at a temperature from about 60° C. to about 140° C. to form a coated SiHy contact lens have a hydrogel coating thereon, wherein the hydrogel coating is covalently attached onto the base coating and is intact and durable, wherein the durability of the hydrogel coating is independent of the optical power or the center thickness of the preformed SiHy contact lens.

2. The method of claim 1, wherein the coated SiHy contact lens having the hydrogel coating thereon passes Sudan Black staining test after being subjected to 30 cycles of digital rubbing treatment, wherein the first and second polyanionic polymers independent of each other are polyacrylic acid, polymethacrylic acid, poly(ethylacrylic acid), poly(propyacrylic acid), poly(acrylic acid-co-methacrylic acid), poly(acrylic acid-co-ethylacrylic acid), poly(acrylic acid-co-propylacrylic acid), poly[ethylacrylic acid-co-(meth)acrylic acid], poly[propylacrylic acid-co-(meth)acrylic acid], poly[ethylacrylic acid-co-propylacrylic acid], or mixtures thereof, wherein the first and second polyanionic polymers independent of each other have a weight average molecular weight of from about 50,000 to about 10,000,000 Daltons.

3. The method of claim 2, wherein the first and second coating solutions independent of each other comprises about 50% or less by weight of any organic solvent, wherein the solution-coating procedure is free of sub-step (c), sub-step (f), or both.

4. The method of claim 2, wherein the first and second coating solutions independent of each other comprises about 50% or less by weight of water, wherein the solution-coating procedure is free of sub-step (c), sub-step (f), or both.

5. The method of claim 2, wherein the first and second coating solutions independent of each other comprises about 50% or less by weight of any organic solvent, wherein the solution-coating procedure comprises sub-step (c), sub-step (f), or both.

6. The method of claim 2, wherein the first and second coating solutions independent of each other comprises about 50% or less by weight of water, wherein the solution-coating procedure comprises sub-step (c), sub-step (f), or both.

7. The method of claim 3, wherein the first and second coating periods of time independent of each other are from about 5 minutes to about 240 minutes, wherein the first and second rinsing periods of time independent of each other are from about 5 minutes to about 240 minutes, wherein the aqueous solution in step (3) has a pH of from about 6.8 to about 9.0.

8. The method of claim 4, wherein the first and second coating periods of time independent of each other are from about 5 minutes to about 240 minutes, wherein the first and second rinsing periods of time independent of each other are from about 5 minutes to about 240 minutes, wherein the aqueous solution in step (3) has a pH of from about 6.8 to about 9.0.

9. The method of claim 5, wherein the first and second coating periods of time independent of each other are from about 5 minutes to about 240 minutes, wherein the first and second rinsing periods of time independent of each other are from about 5 minutes to about 240 minutes, wherein the aqueous solution in step (3) has a pH of from about 6.8 to about 9.0.

10. The method of claim 6, wherein the first and second coating periods of time independent of each other are from about 5 minutes to about 240 minutes, wherein the first and second rinsing periods of time independent of each other are from about 5 minutes to about 240 minutes, wherein the aqueous solution in step (3) has a pH of from about 6.8 to about 9.0.

11. The method of claim 1, wherein the coated SiHy contact lens having the hydrogel coating thereon passes Sudan Black staining test after simulated abrasion cycling treatment, wherein the first and second polyanionic polymers independent of each other are polyacrylic acid, polymethacrylic acid, poly(ethylacrylic acid), poly(propyacrylic acid), poly(acrylic acid-co-methacrylic acid), poly(acrylic acid-co-ethylacrylic acid), poly(acrylic acid-co-propylacrylic acid), poly[ethylacrylic acid-co-(meth)acrylic acid], poly[propylacrylic acid-co-(meth)acrylic acid], poly[ethylacrylic acid-co-propylacrylic acid], or mixtures thereof, wherein the first and second polyanionic polymers independent of each other have a weight average molecular weight of from about 50,000 to about 10,000,000 Daltons.

12. The method of claim 11, wherein the first and second coating solutions independent of each other comprises about 50% or less by weight of any organic solvent, wherein the solution-coating procedure is free of sub-step (c), sub-step (f), or both.

13. The method of claim 11, wherein the first and second coating solutions independent of each other comprises about 50% or less by weight of water, wherein the solution-coating procedure is free of sub-step (c), sub-step (f), or both.

14. The method of claim 11, wherein the first and second coating solutions independent of each other comprises about 50% or less by weight of any organic solvent, wherein the solution-coating procedure comprises sub-step (c), sub-step (f), or both.

15. The method of claim 11, wherein the first and second coating solutions independent of each other comprises about 50% or less by weight of water, wherein the solution-coating procedure comprises sub-step (c), sub-step (f), or both.

16. The method of claim 12, wherein the first and second coating periods of time independent of each other are from about 5 minutes to about 240 minutes, wherein the first and second rinsing periods of time independent of each other are from about 5 minutes to about 240 minutes, wherein the aqueous solution in step (3) has a pH of from about 9.06.5 to about 10.

17. The method of claim 13, wherein the first and second coating periods of time independent of each other are from about 5 minutes to about 240 minutes, wherein the first and second rinsing periods of time independent of each other are from about 5 minutes to about 240 minutes, wherein the aqueous solution in step (3) has a pH of from about 6.8 to about 9.0.

18. The method of claim 14, wherein the first and second coating periods of time independent of each other are from about 5 minutes to about 240 minutes, wherein the first and second rinsing periods of time independent of each other are from about 5 minutes to about 240 minutes, wherein the aqueous solution in step (3) has a pH of from about 6.8 to about 9.0.

19. The method of claim 15, wherein the first and second coating periods of time independent of each other are from about 5 minutes to about 240 minutes, wherein the first and second rinsing periods of time independent of each other are from about 5 minutes to about 240 minutes, wherein the aqueous solution in step (3) has a pH of from about 6.8 to about 9.0.

20. The method of claim 2, wherein the aqueous solution in step (3) is a lens packaging solution, wherein the step of heating is performed by autoclaving the treated silicone hydrogel contact lens immersed in the lens packaging solution in a sealed lens package at a temperature of from about 115° C. to about 125° C. for from about 20 to 90 minutes, wherein the thermally-crosslinkable hydrophilic polymeric material is a partially-crosslinked polymeric material that comprises a three-dimensional network and thermally-crosslinkable groups within the network or being attached to the network, wherein the thermally-crosslinkable hydrophilic polymeric material comprises azetidinium groups and is a partial reaction product of at least one azetidinium-containing polymer with at least one hydrophilicity-enhancing agent having at least one carboxyl, primary amine, secondary amine, or thiol group.

* * * * *

UNITED STATES PATENT AND TRADEMARK OFFICE
CERTIFICATE OF CORRECTION

PATENT NO. : 11,099,300 B2  
APPLICATION NO. : 16/426451  
DATED : August 24, 2021  
INVENTOR(S) : Yongxing Qiu, Hyeju Kim and Ciara Dauenhauer Page 1 of 1

It is certified that error appears in the above-identified patent and that said Letters Patent is hereby corrected as shown below:

In the Claims

Claim 16, Column 48, Line 4 change "about 9.06.5 to about 10." to "about 9.0."

Signed and Sealed this  
Eighth Day of March, 2022

Drew Hirshfeld  
*Performing the Functions and Duties of the*  
*Under Secretary of Commerce for Intellectual Property and*  
*Director of the United States Patent and Trademark Office*